United States Patent [19]
Gartside et al.

[11] Patent Number: 5,220,093
[45] Date of Patent: Jun. 15, 1993

[54] PROCESS FOR PRODUCTION OF OLEFINS FROM MIXTURES OF LIGHT PARAFFINS

[75] Inventors: Robert J. Gartside, Summit, N.J.; Axel R. Johnson, North Babylon, N.Y.

[73] Assignee: Stone & Webster Engineering Corporation, Boston, Mass.

[21] Appl. No.: 863,176

[22] Filed: Apr. 3, 1992

[51] Int. Cl.⁵ .............................................. C07C 5/333
[52] U.S. Cl. ...................................... 585/661; 585/654
[58] Field of Search ........................... 585/655, 660, 661

[56] References Cited

U.S. PATENT DOCUMENTS

| | | | |
|---|---|---|---|
| 3,113,095 | 12/1963 | Braca et al. | 208/155 |
| 4,859,308 | 8/1989 | Harandi et al. | 585/659 |
| 4,921,946 | 5/1990 | Kocal et al. | 585/722 |
| 4,957,617 | 9/1990 | Owen et al. | 208/113 |
| 4,978,440 | 12/1990 | Krambeck et al. | 208/159 |
| 4,988,430 | 1/1991 | Sechrist et al. | 208/150 |

*Primary Examiner*—Anthony McFarlane
*Attorney, Agent, or Firm*—Hedman, Gibson & Costigan

[57] ABSTRACT

Process for catalytic dehydrogenation of a mixture of light paraffins including passing accelerated catalyst with an acceleration gas into a mixing zone for contact with mixed paraffin feedstock, passing the feedstock/catalyst into a reaction zone, separating the effluent from the spent catalyst solids, quenching the effluent and separating and recycling at least a portion of the unreacted light feedstock for use as an acceleration gas to accelerate the fresh catalyst wherein the kinetic residence time from contact of the catalyst and feedstock to quench is between 0.1 and 2.0 seconds.

16 Claims, 13 Drawing Sheets

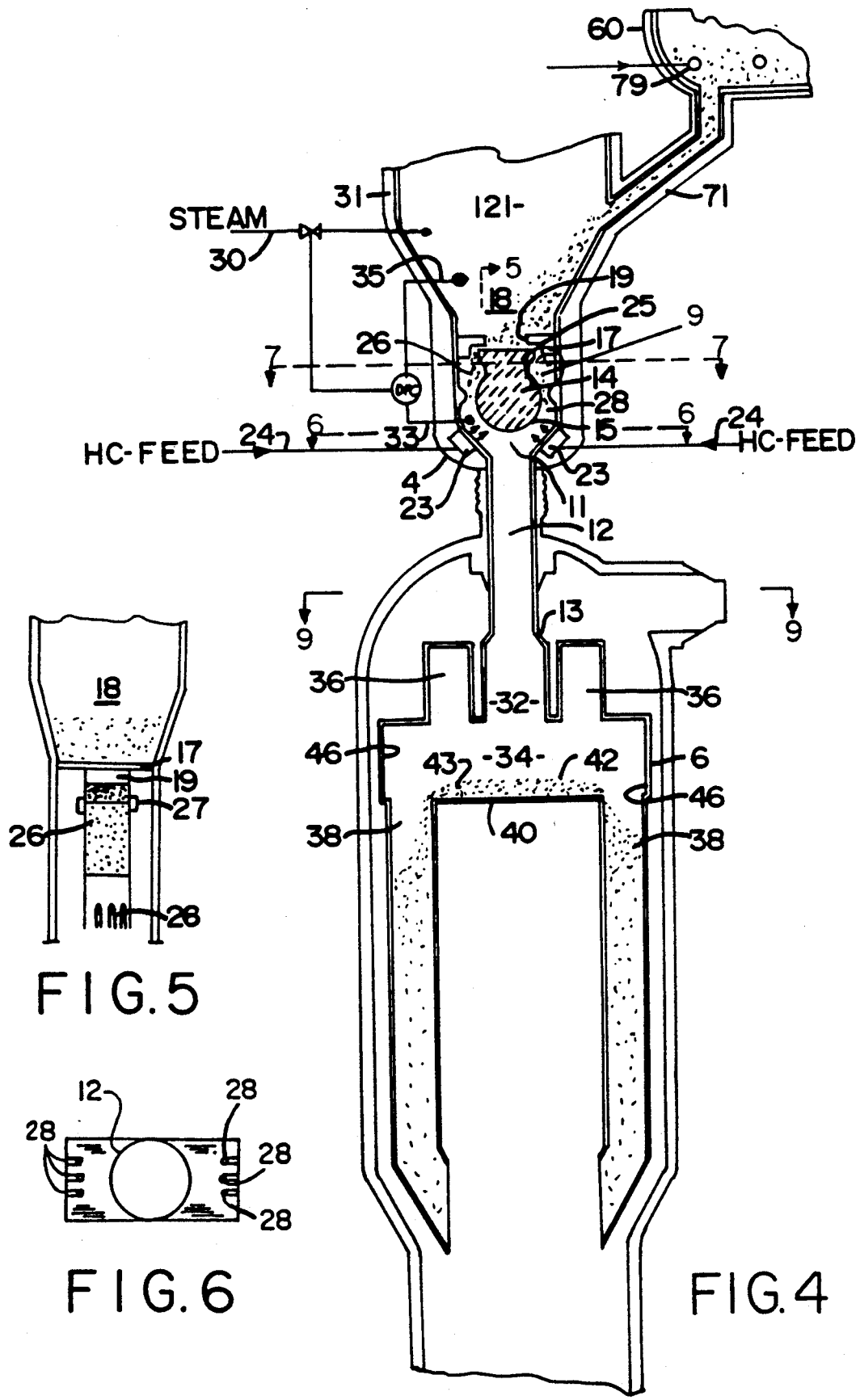

PROCESS FOR PRODUCTION OF OLEFINS FROM MIXTURES OF LIGHT PARAFFINS

REFERENCE TO RELATED APPLICATIONS

This application is related to U.S. patent application Ser. No. 07/757,177, filed Sep. 10, 1991, entitled PROCESS FOR THE DEHYDROGENATION OF LIGHT HYDROCARBONS by Robert J. Gartside and Axel R. Johnson, incorporated herein by reference.

FIELD OF THE INVENTION

The present invention deals with a process for the pyrolytic and catalytic dehydrogenation and cracking of light hydrocarbon mixtures, i.e., two or more paraffins, to the corresponding olefins. Specifically, the present invention relates to a process for catalytically and pyrolytically converting a mixture of light paraffins to olefins in a short kinetic residence time, high temperature fluidized solids environment.

BACKGROUND OF THE INVENTION

Paraffin mixtures occur commonly both in nature and in a refinery. They are present in gas recovery at the oil field itself. LPG, for example, is a mixture of principally C3 and C4 compounds. Field condensate is a mixture of C4 and C5 paraffins that is condensed "in the oil field" as the gas and oil are separated prior to sending the gas and liquid products to separate transportation systems. Paraffin mixtures also occur in refinery separation systems depending upon the degree of separation employed. It is common to find mixed C2/C3 streams within the FCC gas plant for example.

It is desirable on many occasions to further process these mixtures to valuable products including olefins. There are essentially two routes available to react paraffins to olefins and these routes compete with each other. Paraffins can be cracked thermally to produce a mixture that consists of essentially olefins of lower carbon number than the feed, except in the case of ethane where the principal product of thermal dehydrogenation is ethylene. Processing typically occurs at high temperatures and short residence times.

Paraffins can also be reacted catalytically. In these processes, specific catalysts are chosen to allow for the dehydrogenation of the paraffin feed to the olefin of the same carbon number. Processing typically occurs at significantly lower temperatures and longer residence times than thermal cracking (to minimize thermal reactions) and the once through yield of the olefin is strongly influenced by thermodynamic equilibrium.

The products one would achieve by thermal cracking a mixture of paraffins are drastically different from the products one would achieve from catalytically processing the same mixture.

Furthermore, there are significant differences between various paraffins which become important during processing of mixtures. Using propane and ethane as an example, propane is a less refractory molecule (easier to react) than ethane. Attached as FIG. 1 is a plot of the reaction velocity constants for light paraffins as a function of temperature. Note that at any temperature propane will react between two (2) and five (5) times more rapidly than ethane. Attached as FIG. 2 is a plot of the equilibrium curves for the various paraffins. One can see that at any given temperature the propylene/propane ratio will be much higher than the ethylene/ethane ratio, indicating a more favorable equilibrium for propane.

Catalytic dehydrogenation of propane yields propylene. Propane can also be thermally cracked into C2+C1, and propylene product can be cracked or polymerized. These are the degradation reactions. Ethane on the other hand principally dehydrogenates, either thermally or catalytically, but requires more severe conditions in terms of temperature. There is relatively little cracking, i.e., into C1+C1, and little polymerization, i.e., into C4+.

For example, at 1100° F., the thermodynamic equilibrium for propane gives 40% olefins and 60% paraffins while for ethane at the same temperature there is only 14% olefins. Thermal reactions for these paraffins are essentially nonexistent at 1100° F. If, however, the temperature is raised to 1400° F., equilibrium predicts 85% olefins for propylene/propane and 53% for ethylene/ethane. At these temperatures, thermal reactions are significant. At a 1.0 second residence time, 60% thermal conversion would occur for a pure propane stream while at a 0.25 second residence time, only 20% conversion would occur for the same stream. Similarly, 20% thermal conversion of ethane would occur in 1.0 second but just 5% in 0.25 seconds. Therefore, processing a mixture of paraffins in a catalytic dehydrogenation unit leads to feeds achieving considerably different conversions. Within the constraints of equilibrium, it is not possible to simultaneously catalytically dehydrogenate a mixture economically.

This analogy also holds for other light hydrocarbons. For example, with mixtures of propane and butane, butane is easier to react and will have a more favorable equilibrium than propane. The differences in reactivity and equilibrium cause problems in attempts to dehydrogenate paraffin mixtures in "conventional" equipment. Problems are even found in conventional processes when mixed C4 streams are to be processed wherein kinetic and thermodynamic equilibrium differences between isobutane and normal butane exist.

With respect to the yields desired, the prior art provides two options for the processing of paraffin mixtures. If thermal products are desired, the feeds are cracked (in a pyrolysis coil for example) either together or separately. This option maximizes ethylene in the case of ethane/propane feed or mixed products for higher hydrocarbon feeds. For the most part, conversions are high and recycles are low. The exception, however, is ethane For ethane pyrolysis, conversions are limited to 60–70% of the reactor feed in order to minimize fouling. Therefore, in order to fully process an ethane stream, considerable recycle capability must be incorporated.

A pyrolysis plant designed for a mixture of paraffins with carbon number higher than 2, e.g. propane/butane, would have limited recycle capability and thus would have limited capacity to process ethane. This is important in considering the range of potential concentrations of ethane in mixtures as well. If the plant is designed for a 20% ethane/80% propane stream, it would have limited capacity to process an 80/20 ethane/propane stream. The mass flow to the plant, and therefore capacity, would have to be reduced in order to accommodate recycle.

Consider the same ethane/propane mixture, however, with catalytic yields (high propylene in this case) desired. Two separate trains of conventional processing are required. The mixed feed would first require separation of the paraffins, then individual processing of the paraffins, possibly including product separation, and finally combination of the effluents. Ethane cannot be processed economically in a fixed bed catalytic dehydrogenation process since conversions would be on the order of 20% and thus would result in very high recycle rates. This would require substantial separation system energy and capacity, substantially increasing cost. For the ethane/propane mixture of the example, a combination of ethane cracking coils and propane dehydrogenation units are required. For mixtures of paraffins with a higher carbon number, separate dehydrogenation units would probably be required. It is also true that once a commitment is made to proceed by dehydrogenation, there is no option for cracking.

The differences in conversion at similar operating conditions creates problems when coprocessing mixtures. Here, it should be noted that co-processing two feeds in the same reactor at the same time is distinct from co-processing feeds in parallel reactors, each of which operates at separate conditions. Since only one set of conditions (temperature, pressure, residence time, catalyst type, etc.) can exist in a single reactor at any one time, both feeds see that set of conditions. This set may or may not be optimal for one but given the difference in kinetics and equilibrium, will certainly not be optimal for both.

In order to co-process two hydrocarbons in the same piece of equipment, one feed must be overreacted and the other underreacted, or the lighter one must be reacted to an economic level and the heavier one severely overreacted leading to a rapid catalyst fouling. To react the heavier feed optimally would result in only small conversion levels for the light feed which would represent a significant underutilization of the equipment, and generate huge recycles within the plant.

Of the possible options for the known methods set forth above, there is really no practical option. Operation at economically acceptable conversions of the heavier feed underutilizes the light feed and operation at economically acceptable conversions for the light feed results in rapid catalyst fouling due to overreaction of the heavy feed. There may be some exceptions to this when processing mixtures with very high concentrations of the heavier feed component.

In fixed bed processes, when trying to operate the short times preferred for dehydrogenation, a shallow bed is required and typically a radial flow bed is used. In a radial flow bed, solids are located in a thin annulus, vertically oriented within the bed. The feed is introduced in a complicated internal distribution system over the bed and then passes through the thin annulus. By fixing the solids in the annulus, the maximum surface area for flow is attained in a minimum vessel diameter. Flow area determines capacity since gas velocity must be low to avoid high pressure drops. There is no possibility for heat addition and/or removal from such a reactor. Heat for the endothermic dehydrogenation reaction is provided by preheating the feed which contains significant quantities of diluent acting as a heat carrier.

Tubular reactors can provide some heat addition and/or removal but are very limited in their capacity to do so. In order to get short residence times, catalyst depths (or tube lengths in this case) must be limited given the low gas velocity required to avoid high pressure drop, due to the detrimental effect of absolute pressure on conversion (equilibrium limit). In order to avoid hot tube walls and excessive reaction at the wall, the temperature driving forces are held low. Thus, the total heat that can be transferred through the wall of the tube is low since it is proportional to the tube surface area and temperature difference. In order to satisfy even minimal heat removal or addition requirements, a great many small diameter tubes having high surface to flow volume in each tube are required, leading to an extremely complex distribution system into and out of the tube banks.

The only option for dehydrogenating paraffin mixtures using conventional processing equipment is to run separate reaction systems in parallel. This however requires separate feed preparation and product recovery equipment for each feed component, adding significantly to the cost of such a unit.

SUMMARY OF THE INVENTION

Therefore, it is an object of the present invention to provide a process for the simultaneous dehydrogenation and thermal cracking of light paraffin mixtures to olefins. It is also an object to provide a process to efficiently dehydrogenate and thermally crack mixtures of light paraffins with low recycle requirements and high unit capacity. It is a further object to provide such a process which utilizes short kinetic residence times in a high temperature fluidized solids environment.

These and other objects are realized by the present process for dehydrogenation of light paraffin mixtures of lower number and higher paraffinic components, comprising introducing hot, fresh catalytic solids into an acceleration zone and accelerating the solids with an acceleration gas; passing the accelerated catalytic solids from the acceleration zone into a mixing zone; introducing a mixed paraffin feedstock into the mixing zone, and into contact with the accelerated catalytic solids; passing the feedstock/catalyst mixture out of the mixing zone and into a reaction zone where the feedstock is converted to an effluent; passing the effluent/catalyst solids mixture into a separation zone; separating the catalyst solids from the effluent gas in the separation zone; quenching the effluent once it leaves the separation zone; separating the unreacted light feedstock component of the effluent from the product gases; and: recycling the unreacted light feedstock component back to the acceleration zone for use as acceleration gas to first contact the fresh, hot recycled catalyst to allow for dehydrogenation and thermal cracking of the recycled light feedstock component to a greater degree than the new mixed feedstock, resulting in dehydrogenation of each of the light paraffins.

The present process is achieved using a QC (quick-contact) fluidized solids cracking apparatus employing a short residence time having a unique operating window suited to exploit the co-processing of paraffins having different carbon numbers or reactive characteristics. Suitable apparatus are described in U.S. Pat. Nos. 4,919,898 and 4,814,067, both to Gartside et al. A short residence time separator is described in U.S. Pat. No. 4,433,984 to Gartside et al. All cited patents are incorporated herein by reference.

The QC reactor provides an advantage in that it can be used with various product slates and can process different gas mixtures in a single unit. The QC reactor is also able to process light paraffins absent of or with a minimal diluent flow, resulting in a high capacity process when compared to conventional systems.

The benefits of the QC reactor for dehydrogenation and thermal cracking of paraffin mixtures include a combination of higher temperature/shorter time reactions, a circulating catalyst solids system that allows continuous heat input plus catalyst regeneration, and the use of an acceleration zone for a high recycle conversion cracking/dehydrogenation zone.

The QC system also has advantages when catalytic yield slate is desired and/or some thermal products are desirable, or when a changing feed composition is anticipated.

As set forth above, differences in the reaction rates and thermodynamic equilibrium result in different "optimum" processing conditions for different paraffins. A short residence time circulating solids reactor system is used to take advantage of the unique operating window and achieve highly selective yields at high conversion per pass of a mixture of paraffins.

The examples presented throughout the present application are for an ethane/propane system but apply equally well to mixtures of other paraffins. This is demonstrated by the ratio of reaction velocity constants and equilibrium presented in Table 1.

product quench utilized by the QC reactor avoids degradation of the olefin products from the heavier feed.

For mixed feed cases it has been found that the economic optimum processing point is essentially complete conversion of the heavier feed component and the related optimum conversion for the lighter feed component. This eliminates recycle of the heavy feed component. The essentially complete conversion of the heavier feed component is not optimum from its own selectivity point of view, however, it is favored from an economic standpoint when processing mixtures.

If, for example, the specific optimum temperature for propane dehydrogenation is 1350° F. to achieve 85% conversion per pass, operation with ethane alone under these conditions would yield negligible reaction (about 20% conversion). This would be uneconomic for ethane and the option would be to run individual reaction systems for each.

The QC system could, however, be operated at 1450° F. where the propane would be completely converted (thermally and catalytically) to propylene plus some thermal products (ethylene and methane). The ethane would be converted both thermally and catalytically at

TABLE 1

| | | CRACKING RATE (thermal) | EQUILIBRIUM (@ 1 ATM) (mol ratio) | % Olefin |
|---|---|---|---|---|
| $C_2H_6$ | (@ 1300° F.) | 0.176 | (.45 $C_2H_4$:.55 $C_2H_6$) | 45 |
| $C_3H_8$ | | | (.80 $C_3H_6$:.20 $C_3H_8$) | 80 |
| $C_3H_8$ | (@ 1100° F.) | 0.27 | (.48 $C_3H_6$:.52 $C_3H_8$) | 48 |
| N—$C_4H_{10}$ | | | (0.05 $C_4H_6$:0.57 $C_4H_8$:0.38 $C_4H_{10}$) | 57 |
| I—$C_4H_{10}$ | (@ 1100° F.) | 0.59 | (0.68 $C_4H_8$:0.32 $C_4H_{10}$) | 68 |
| N—$C_4H_{10}$ | | | (0.05 $C_4H_6$:0.57 $C_4H_8$:0.38 $C_4H_{10}$) | 57 |

Also important to the product distribution is the type of cracking regime that controls the process. Although the dehydrogenation products are necessarily olefins and hydrogen, the thermal products vary considerably, as shown in Table 2.

TABLE 2

Primary Product Distributions (Wt per Wt Reacted)

| | CATALYTIC | | THERMAL | |
|---|---|---|---|---|
| ETHANE | $H_2$ | 0.067 | $H_2$ | 0.067 |
| | $C_2H_4$ | 0.933 | $C_2H_4$ | 0.933 |
| PROPANE | $H_2$ | 0.045 | $H_2$ | 0.016 |
| | $C_3H_6$ | 0.955 | $CH_4$ | 0.237 |
| | | | $C_2H_4$ | 0.415 |
| | | | $C_3H_6$ | 0.332 |
| I BUTANE | $H_2$ | 0.034 | $H_2$ | 0.012 |
| | I—$C_4H_8$ | 0.966 | $CH_4$ | 0.177 |
| | | | $C_2H_4$ | 0 |
| | | | $C_3H_6$ | 0.466 |
| | | | I—$C_4H_8$ | 0.345 |
| N-BUTANE | $H_2$ | 0.037 | $H_2$ | 0.17 |
| | N—$C_4H_8$ | 0.888 | $CH_4$ | 0.142 |
| | $C_4H_6$ | 0.075 | $C_2H_4$ | 0.467 |
| | (@ equilibrium @ 1100° F.) | | $C_3H_6$ | 0.239 |
| | | | N—$C_4H_8$ | 0.159 |

A QC type unit is not limited by heat input, therefore, it can process the higher heat required for the heavier feed. Furthermore, since the catalyst is circulated and regenerated essentially every 20 minutes (time for a solid to make a complete cycle of the unit), catalyst fouling due to overreaction is also not a consideration. Additionally, short kinetic residence times including 60% conversion per pass to ethylene. A fixed bed reaction system cannot do this due to the stringent demands on heat input which cannot be satisfied externally, and the high catalyst fouling. Attempts to do so at long residence time would lead to severe degradation of the propylene formed from the propane.

The differences in the equilibrium curves of FIG. 2 and the kinetic reaction rates of FIG. 1 provide the basis for determining optimal conditions.

There is a second aspect relating to the QC reactor itself. The QC system as designed is particularly well suited for such a process. A mixed feed can be fed to the main reaction point and the heavier feed component essentially completely converted. The light feed component recycle can be then used as an acceleration gas in the QC solids feed system. Contact of the recycle gas with the hottest catalyst first allows the recycle gas to exploit the preferred operating conditions for that feed component (i.e. highest temperature).

It should be noted that within the practical limitations of a reactor design, there may be some limits on the absolute amount of recycle light hydrocarbon that can be utilized as acceleration gas. In certain cases it may be economical to process the excess portion of the recycle in a separate QC reactor or in a conventional furnace for ethane. Pyrolysis processing of a portion ethane recycle is still economic since the major product from both thermal and catalytic processing is the conjugate olefin (ethylene).

The present process efficiently dehydrogenates a mixture of light hydrocarbons and also achieves significant improvements in process economics. Not only is the reactor capacity greatly increased but product gas compression is reduced and separation energy and equipment are reduced.

The choice of catalyst is again dependent upon the selectivity and processing conditions desired. Although most all catalyst groups described can be utilized with the present invention, moderate and high activity catalysts, as defined below, are preferred. More active catalysts will give more dehydrogenation character to the yields; less active catalysts will give more thermal character to the yields. The system can take advantage of the different catalysts since it can operate at high heat input and short residence time.

The catalyst solids comprise an inert carrier such as amorphous or kaolin clay, silica, or alumina impregnated with one or more catalytically active ingredients. It is known in the field that certain metals and their oxides act as catalysts for the dehydrogenation of paraffins. Primarily, these metals are from the noble metal group or the transition metal group as defined by the periodic table of elements. Examples of noble metals include iron (Fe), nickel (Ni), palladium (Pd), and platinum (Pt). Examples of transition metals include vanadium (V), chromium (Cr), and manganese (Mn). It is also known in the field that certain alkali compounds, such as potassium oxide ($K_2O$), are beneficial in promoting the activity of the metal oxides as catalysts. Further, other elements such as tin (Sn), and lead (Pb), have exhibited catalytic activity in their oxide form. The catalyst may further comprise an aluminosilicate zeolite.

The feedstock, comprising the paraffin mixture, is preheated and rapidly mixed with the preheated catalyst solids which have been accelerated into the top of reactor with a minimal amount of diluent or, preferably, recycled feed component. This combined stream is passed down through the reactor where the hydrocarbon undergoes thermal and catalytic reactions including dehydrogenation. The operating conditions of the reactor are generally from about 900° F. to about 1600° F. at a pressure from about 10 psig to about 100 psig with a hydrocarbon residence time from the point of feedstock introduction to the point of quench of from about 0.1 seconds to about 2.0 seconds, shorter residence times requiring higher temperatures.

The effluent produced from this process flows through a separator where the combined product and diluent are rapidly separated from the catalyst solids and then quenched by direct introduction of a quench medium to freeze the reaction. The catalyst solids from the separator are stripped of residual hydrocarbon, regenerated and reheated to a temperature of from about 1300° F. to 1800° F. and returned to the top of the tubular reactor. The continuous regeneration of the catalyst provides higher intrinsic levels of activity for the QC systems compared to fixed bed systems where there is no continuous regeneration.

The total residence time in the system is a function of unit geometry and the volume flow of the feedstock reaction mixture. Residence times in the order of 200 milliseconds can be achieved at capacities equivalent to those for commercial reaction systems. Residence times greater than 200 milliseconds are possible by simply lengthening the reactor or reducing the throughput.

BRIEF DESCRIPTION OF THE DRAWINGS

The following figures are intended to aid in the understanding of the present invention without limiting the invention in any manner whatsoever, wherein:

FIG. 4 is an enlarged sectional view of the reactor and cracked gas/solids separator of the present invention;

FIG. 5 is a sectional view through line 5—5 of FIG. 4;

FIG. 6 is a plan view through line 6—6 of FIG. 4;

DETAILED DESCRIPTION OF THE INVENTION

The present process provides an advance in the art of producing olefins from mixtures of light hydrocarbons wherein the mixtures need not be separated prior to dehydrogenation and can be processed by thermal cracking or catalytic dehydrogenation in the same unit.

For the purposes of explanation, the description will address mixtures of propane and ethane although it is understood that the process is equally applicable to mixtures of other light hydrocarbons, i.e., paraffins of five (5) or fewer carbon atoms.

Figure 12:
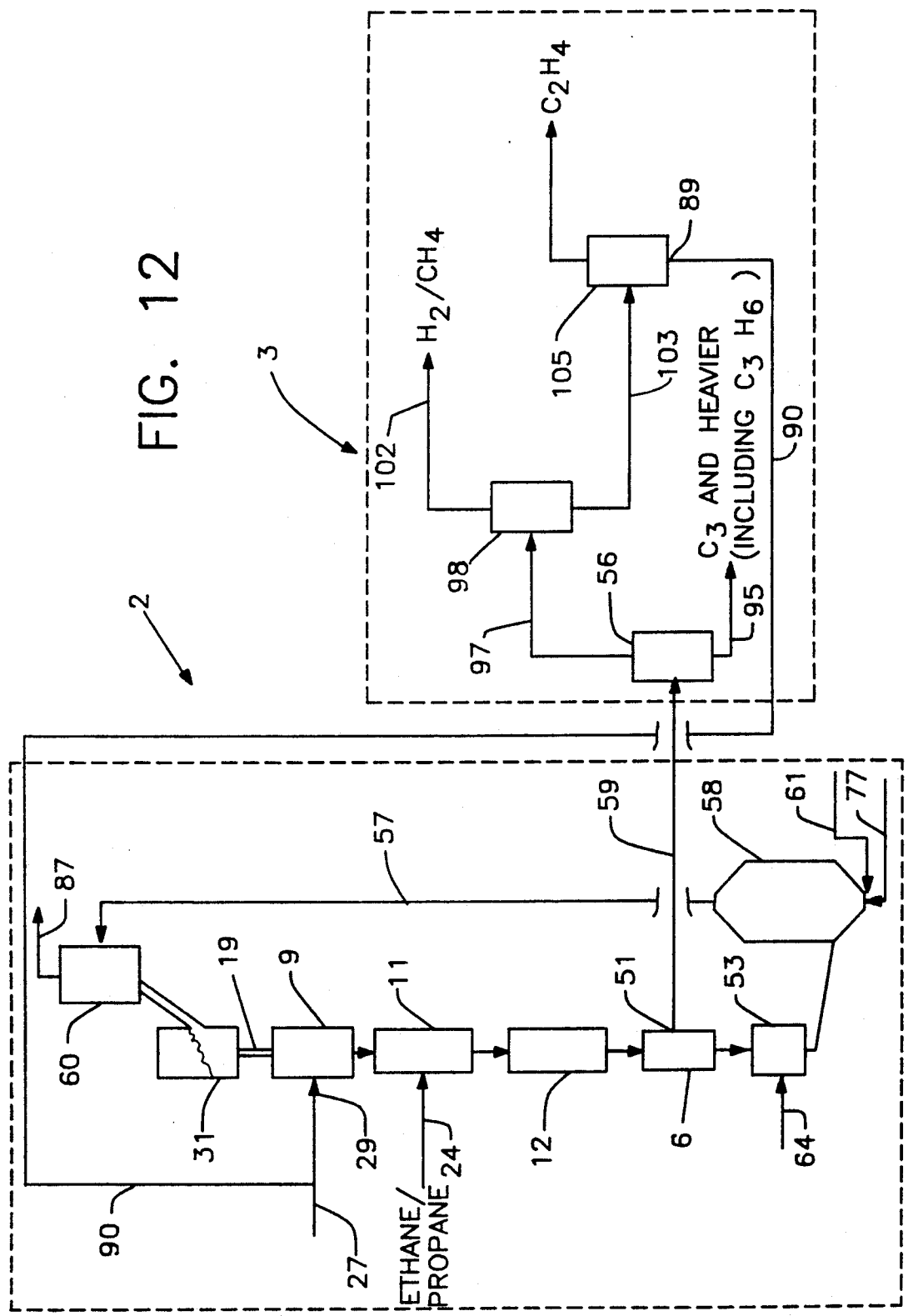
FIG. 12 is a block diagram of the QC process for mixtures of light paraffins.

An overview of the present process is set forth in FIG. 12 comprising a block diagram. In the diagram, catalyst solids are fed from a catalyst control hopper 31 through catalyst inlet passages 19 into the acceleration zone 9. In the acceleration zone 9, the catalyst solids are accelerated with an acceleration gas which enters the acceleration zone 9 through acceleration gas nozzles 29. The acceleration gas can be an inert gas, such as steam, which is fed to the nozzles 29 from line 27 or, preferably, the recycled, unreacted light component of the feedstock (i.e ethane) delivered to the nozzles 29 from recycle feed line 90. The accelerated catalyst solids pass into the reactor mixing zone 11 where the feedstock is introduced through a feedstock delivery line 24. The catalyst/feedstock mixed phase passes from the mix zone 11 into the reaction zone 12 and further into a separator 6 where the catalyst solids and effluent are separated.

Once separated from the effluent in the separator 6, the spent catalyst solids move to a stripping zone 53 where stripping gas, i.e. steam, is introduced through a stripping gas nozzle 64. The stripped solids are passed to an entrained bed heater 58 where the catalyst is regenerated. Air and fuel for regeneration are provided through nozzles 77 and 61, respectively. The regenerated catalyst solids and flue gases are brought up along lift line 57 to a regenerated solids vessel 60 where the flue gases are removed via line 87 and the solids are held for feed into the control hopper 44.

The effluent passes from the separator 6 through line 59 from the catalytic dehydrogenation system 2 into separation system 3. There are many variations possible for separating reaction components. One such variant (shown in FIG. 12 as separation system 3) initially separates the reaction effluent into heavier reaction components and lighter components in separator 56. The heavier products leave (to further separation) via line 95. The lighter components containing the remaining unreacted light hydrocarbon feed, pass via line 97 to separator 98, where essentially fuel gas components are removed via line 102. The lighter feed and its conjugate olefin pass via line 103 to separator 105 where separation takes place. Unreacted light hydrocarbon is then recycled back to the catalytic dehydrogenation system 2 via line 90 where it enters the acceleration zone 9.

Figure 1:
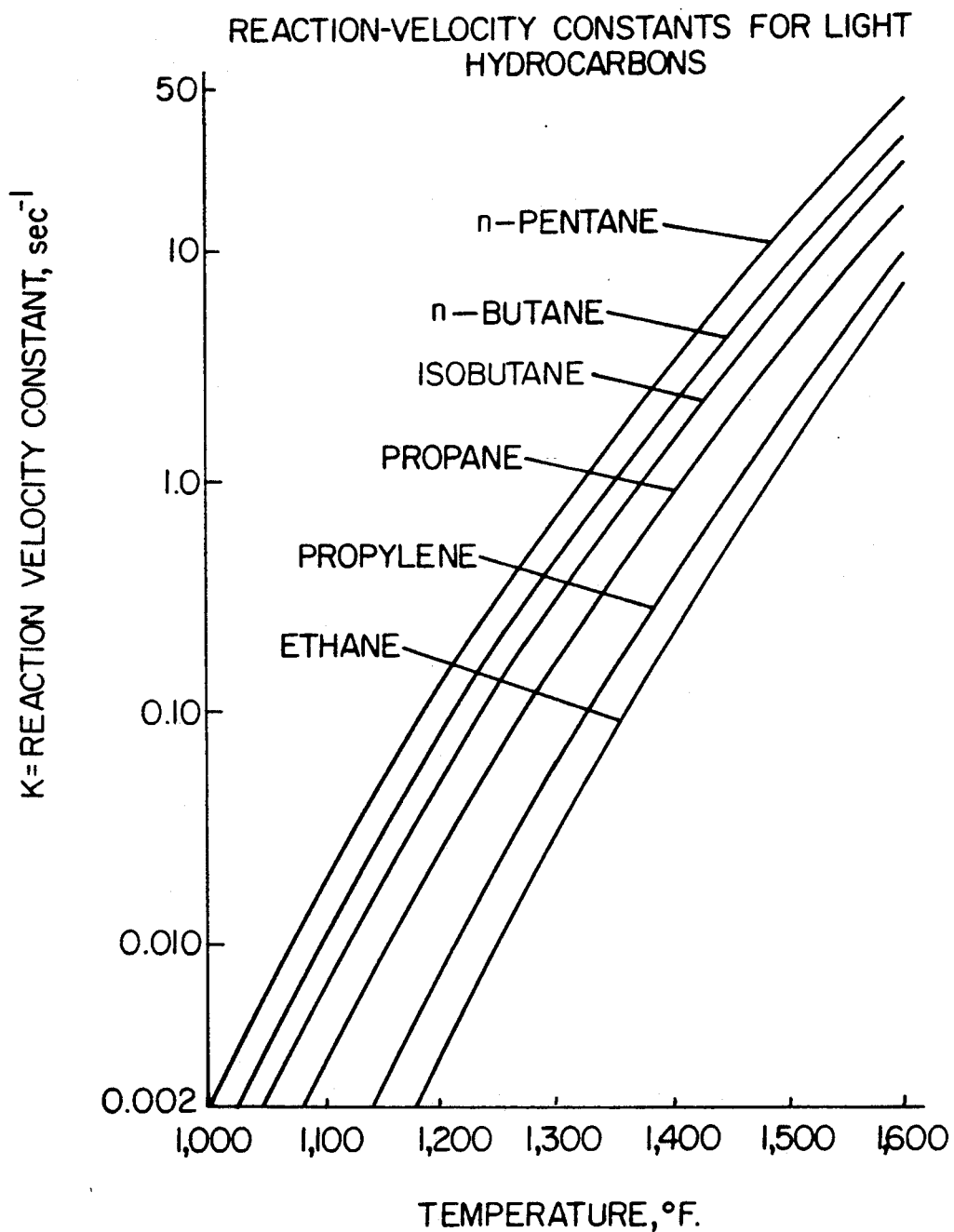
FIG. 1 is a graph of reaction velocity constants for light hydrocarbons.
Figure 2:
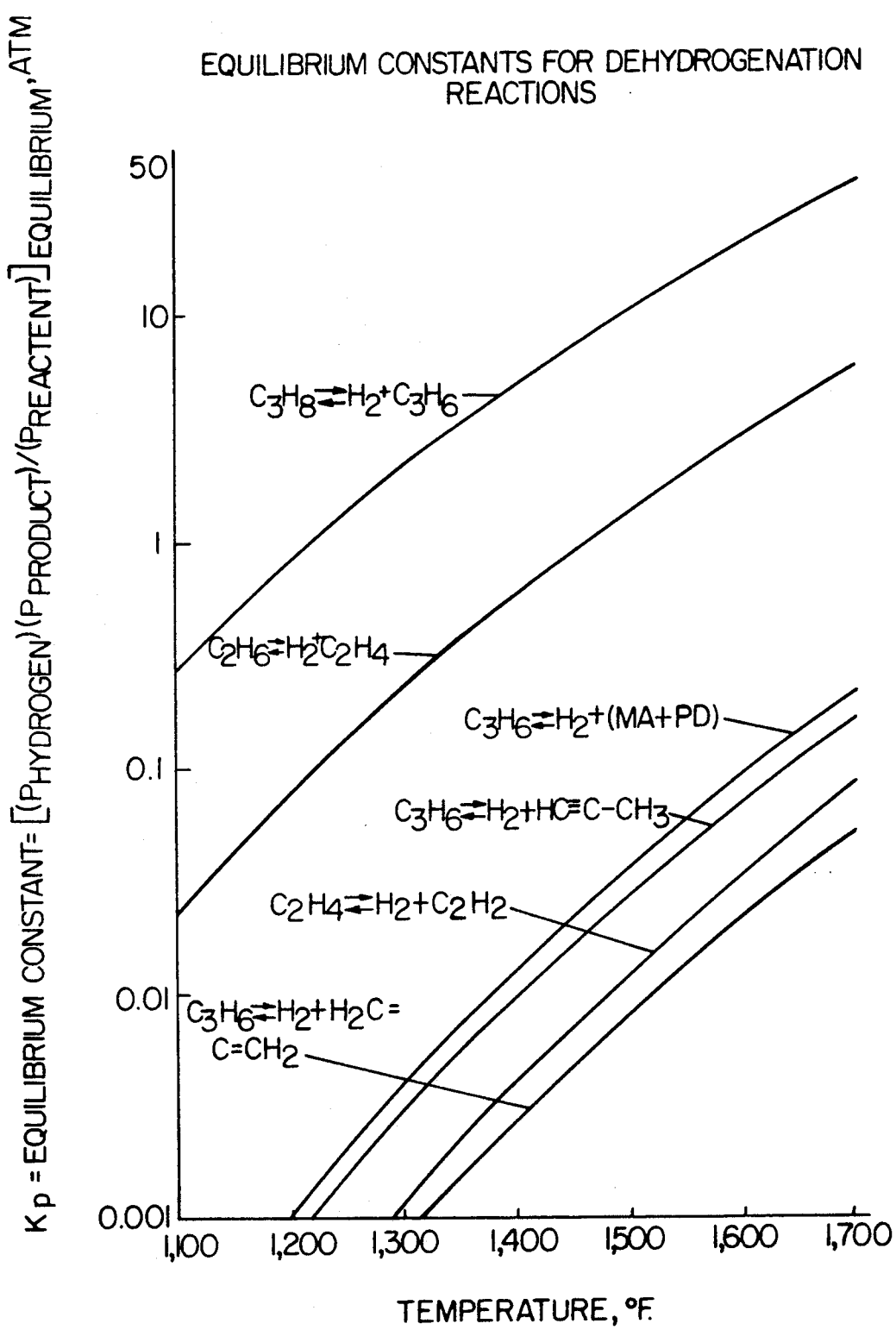
FIG. 2 is a graph of equilibrium constants for dehydrogenation reactions.
Figure 3:
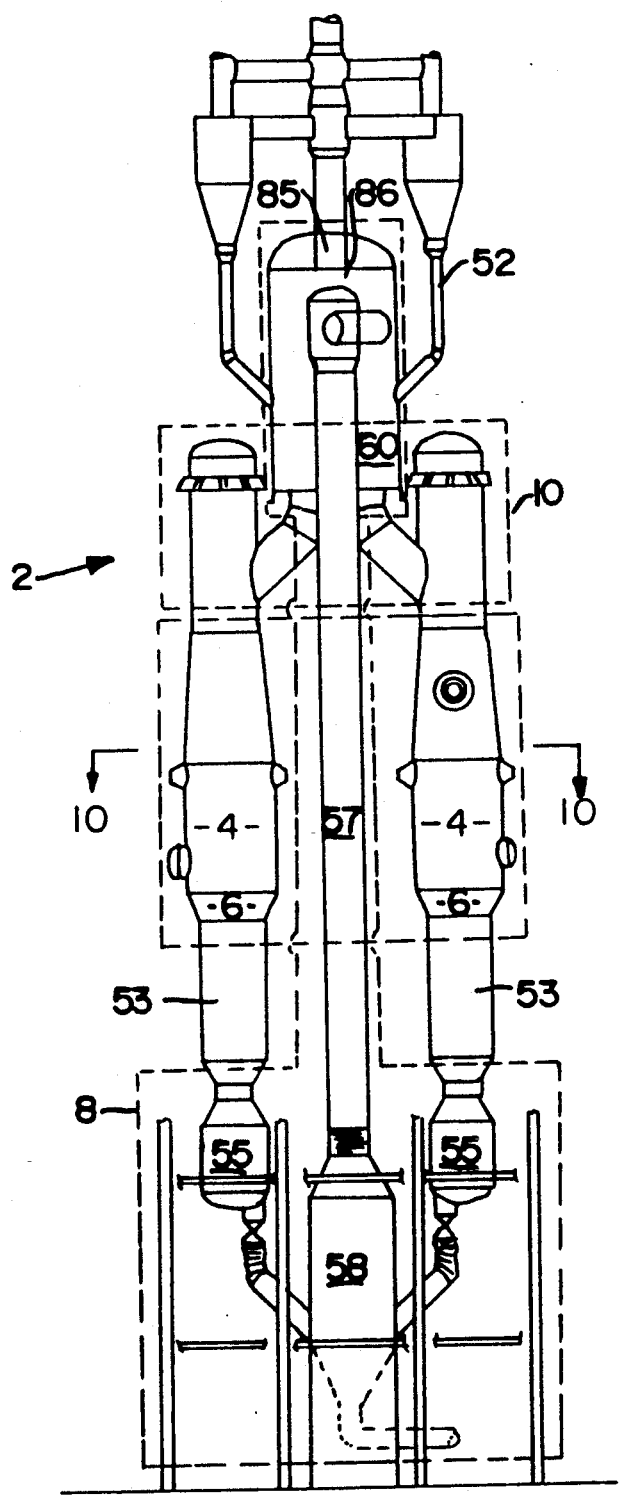
FIG. 3 is an elevational view of the preferred QC system employed by the present process.

As seen in more detail in FIG. 3, the fluidized catalyst dehydrogenation system 2 is comprised essentially of a reactor system 4, a solids regeneration assembly 8 and a solids delivery system 10.

Figure 9:
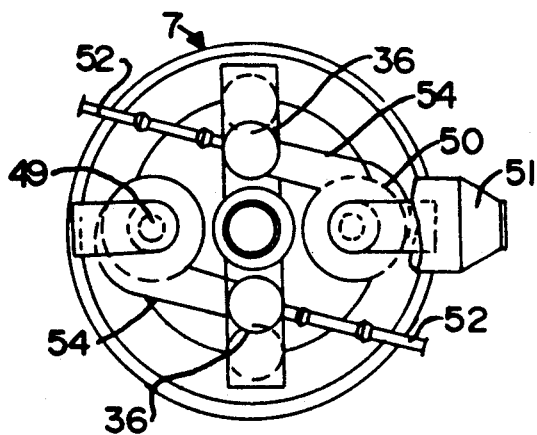
FIG. 9 is a sectional plan view through line 9—9 of FIG. 4.
Figure 10:
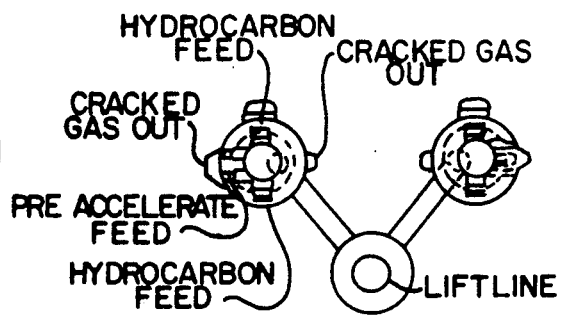
FIG. 10 is a sectional view through line 10—10 of FIG. 3.

The reactor system 4, best seen in FIG. 4, includes an acceleration section 9, a convergent mixing section 11, an elongated reaction section 12, a divergent section 13 downstream of the elongated reaction section 12, a separator 6 and quench system 7 (shown in FIG. 9). The acceleration section 9 and mixing section 11 are formed with a plug section 14 shown in cross-section in FIG. 4 as having an arcuate lower surface 15. A horizontally disposed plate 17 is arranged over the plug section 14 in spaced relationship with the plug section 14 to form catalyst solids inlet passages 19 to the interior of the acceleration section 9. The solids inlet passages 19 are configured in cross-section with a right angle turn and terminate in rectangular openings 25 through which the particulate solids enter the acceleration section 9 in the form of a curtain of catalyst solids 26, as best seen in FIG. 5. Thus, the solids inlet passages 19 are arranged normal to the reactor centerline and thereafter turn at a right angle to terminate in openings 25 parallel to the reactor centerline. The horizontal openings 25 are directly above each hydrocarbon feed inlet 28. Venturi configured passages extend from the solids inlet passages 19 to the mixed hydrocarbon feed inlets 28.

Figure 7:
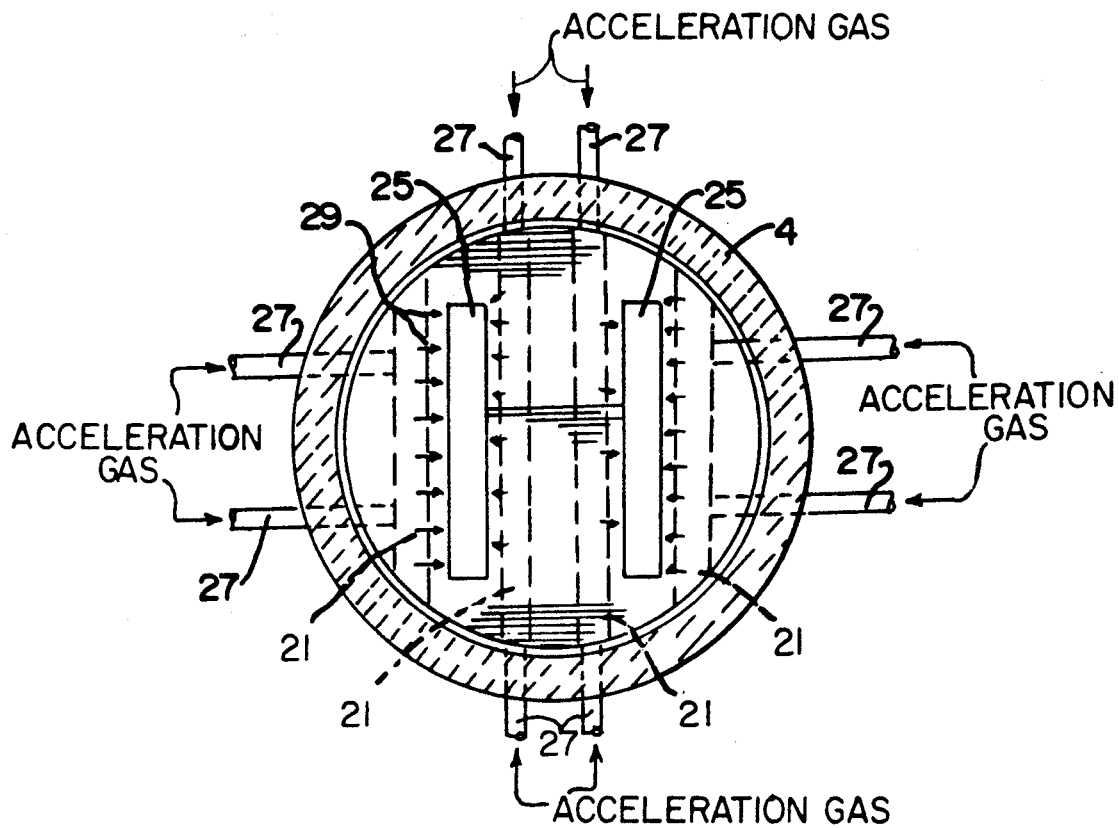
FIG. 7 is a sectional plan view through line 7—7 of FIG. 4.
Figure 8:
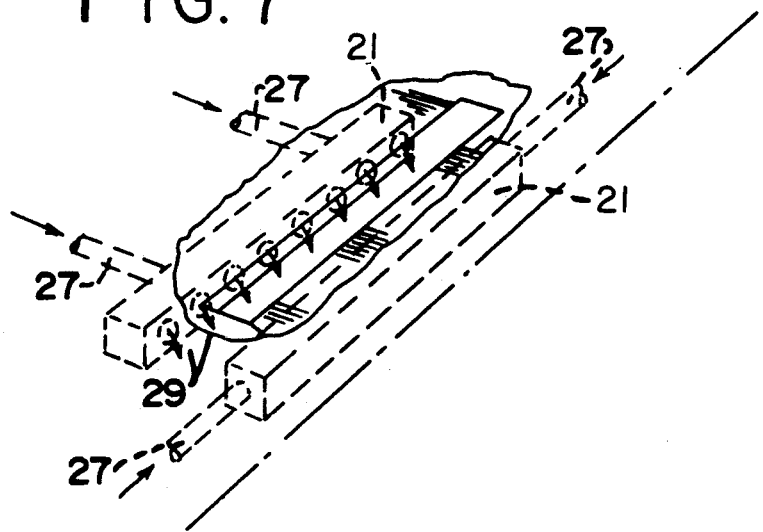
FIG. 8 is partial view of the solids inlet to the reactor shown in FIG. 7.

Plenums 21, best seen in FIGS. 7 and 8, are arranged along each longitudinal edge of the horizontal opening 25 to deliver acceleration gas through nozzles 29 into the curtain of solids 26 passing through the horizontal openings 25. A gas delivery line 27 is provided to deliver inert diluent, usually steam, and delivery line 90 is provided to deliver recycled unreacted light feed component when available, under pressure to the nozzles 29. The nozzles 29 are arranged at a downward angle of 45° to the horizontal. The acceleration gas is delivered to the plenums 21 at pressures of 3 to 5 psi above the pressure in the reactor and discharges through the nozzles 29 at that same relative pressure at a velocity of about 150 feet per second. The acceleration gas accelerates the flow of solids from a nominal three (3) to six (6) feet per second (fps) through the horizontal openings 25 to approximately 50 fps for the mix of solids and acceleration gas. The volume of the acceleration zone 9 is defined by the degree of reaction desired in the acceleration zone 9.

The use of recycled, unreacted light feed component as the acceleration gas is especially suitable in reacting light paraffin mixtures wherein the system is set for 100% conversion of the heavy feed component and the light feed component is only partly reacted. The use of the unreacted light feed component as the acceleration gas subjects the recycled unreacted light feed component to the harshest conditions, i.e., hot, fresh catalyst, to react the light feed component as much as possible prior to contact with the fresh feedstock mixture.

The fresh mixture feed inlets 28 are located on the reactor wall arranged either normal to the solids curtain 26 or at an angle upwardly of 30° into the solids curtain 26. The feedstock is delivered to a manifold 23 through a line 24. The feed inlet nozzles 28 are fed with the paraffin mixture feedstock from the manifold 23. As seen in FIG. 4, the feed inlet nozzles 28 are diametrically opposed from each other in the same horizontal plane. The mixing zone 11 of the reactor is rectangular as seen in FIG. 6 with the configuration making a transition to a tubular reactor at the elongated reaction section 12.

The feedstock entering the mixing zone 11 through nozzles 28 immediately engages the accelerated solids curtain 26 and the desired mixing of feed and hot particulate solids occurs. With the opposing set of nozzles 28, the feedstock and entrained solids from the solids curtain 26 will be directed by the arcuate contour 15 of the plug section 14 and impact with each other at approximately the vertical centerline of the mixing zone 11. When a gas-liquid mixed phase light paraffin mixture is fed through the nozzles 28, the nozzles 28 are arranged at an angle normal or 90° to the solids curtain 26. When the mixed hydrocarbon feedstock is a gas, the nozzles 28 are arranged at an upwardly directed angle of 30° into the solids curtain 26.

The quantity of solids entering the acceleration zone 9 of the reaction system through the horizontal inlets 19 is controlled in large part by the pressure differential between the mixing zone 11 of the reaction system and the chamber 121 above the bed of solids 18 in the solids control hopper 31 directly above the horizontal inlets 19. Generally, however, the ratio of catalyst to feed is from about 5:1 to about 100:1. Pressure probes 33 and 35 are located respectively in the mixing zone 11 of the reaction system and the control hopper chamber 121 to measure the pressure differential. Gas (steam) under pressure is delivered through a line 30 to the control hopper chamber 121 to regulate the pressure differential between the mixing zone 11 of the reaction system and the control hopper chamber 121 to promote or interrupt flow of the solids from the solids control hopper 31 to the mixing zone 11 of the reaction system 4. A detailed description of the process of regulating the solids flow is found in U.S. Pat. Nos. 4,459,071 and 4,453,865 that are incorporated herein by reference.

The solids enter the acceleration zone 9 at a temperature between 1300° F. and 1800° F. through horizontal inlets 19 in the form of a solids curtain 26. The solids then contact the acceleration gas from plenum 21 and nozzles 29. The acceleration gas accelerates the solids curtain 26 to approximately 50 fps in the acceleration zone 9. Acceleration of the catalyst solids promotes improved mixing in the mixing zone 11 and enhanced heat transfer between the main feedstock and the solids-acceleration gas mixture in the mixing zone 11.

The acceleration gas can either be an inert diluent such as steam delivered from line 27 or can be the unreacted light feedstock portion of the feed mixture separated from the product gases and delivered from line 90. If the recycled, unreacted light feed component is used, the volume of the acceleration zone 9 is so designed to achieve a desired conversion of the recycled lighter feed prior to the contact with the main feed mixture in the mixing zone 11.

The fresh mixed hydrocarbon feedstock enters the mixing zone 11 of the reaction system at a temperature of 60° F. to 1000° F. and is elevated to a cracking temperature of 900° F. to 1500° F. by contact with the hot catalyst solids. Cracking and/or dehydrogenation of the feedstock proceeds through the mixing zone 11 and elongated reaction zone 12. Thereafter, the combined effluent, including the product gases and unreacted light feed component, and entrained catalyst solids discharge to the separator 6. Following the separation of the catalyst solids from the effluent, the effluent gases are quenched. The residence time from feedstock entry into the reaction system, i.e. entry into the mixing zone 11, to the point of quench at the exit of the separator 6 of the reaction system 4 is from about 0.01 to about 2.0 seconds. This time represents the time of intimate contact between the catalyst and the feedstock and is called the kinetic residence time and is dependent on various factors including the temperature in the reaction zone 12 and the activity of the catalyst.

As best seen in FIG. 4, the separator 6 is comprised of a mixed phase inlet 32, a horizontal chamber section 34, a plurality of cracked gas outlets 36 and catalyst solids outlets 38. The separator 6 is an improvement on the solids-gas separator described in U.S. Pat. No. 4,433,984, which is incorporated herein by reference. The basic principles relating to relative diameters (Di, Dog, Dos), chamber height (H) and length (L) recited in U.S. Pat. No 4,433,984 again pertain. However, the separator 6 is arranged in combination with the elongated cracking zone 12 and a divergent section 13 of the reaction system 4.

The divergent section 13 of the reaction system 4 terminates in the separator mixed phase inlet 32 which is centrally disposed at the top of the horizontal section 34. As a result of the configuration of the composite reaction system including the separator 6, a solids bed 42 develops on the floor 40 of the horizontal section 34 with the cross-sectional profile 43 of the bed 42 forming a curvilinear arc over which the mixed phase gas and solids travel. The expansion of solids and cracked gas in the divergent section 13 enhances heat transfer and changes the velocity of the solids-gas mixture entering the separator 6 to aid separation.

The spent solids are sent to the lateral ends 46 of the horizontal section 34 and discharge downwardly through the solids outlets 38. The cracked gases follow a 180° path and after initial separation from the solids discharge through gas outlets 36 that are located on the top of the horizontal section 34 intermediate the lateral ends 46. The plurality of solids outlets 38 and gas outlets 36 provide simultaneously for both minimum time in the separation zone 6 and maximum solids-gas separation.

The gas outlets 36 lead directly to conventional cyclone separators 50, best seen in FIG. 9. The entry line 54 to each cyclone separator 50 is arranged at an angle of 90° to the gas outlet 36 with the cyclone separators 50 vertically disposed in the system. The cyclone separators 50 serve to collect the remaining entrained catalyst solids from the effluent discharged from the separator 6. A dipleg line 49, returns the particulate catalyst solids to the regeneration assembly 8. In practice, the separator 6 separates 95 to 99% of the catalyst solids from gas-solids mixtures having dust loadings of 0.2 to 0.3 pounds of solid per cubic foot of gas where the average particle size of the catalyst solids is 90 microns.

Each cyclone entry line 54 extending from the cracked gas outlet 36 to the cyclone 50 is provided with a direct quench line 52. Quench oil, usually the 100°–400° F. cut from a downstream distillation tower, is introduced into the cyclone 50 through the direct quench line 52 to terminate the reactions of the cracked gas. Preferably, 0.1 to 0.3 gallons of quench oil are introduced upstream of the cyclone 50 for every pound of cracked gas.

The product gases and unreacted feed component are sent for downstream processing along line 59 through the gas outlet 51. Processing of the effluent includes separation of the unreacted light feed component from the product gases and recycle of the unreacted component to the acceleration zone 11 along recycle line 90.

In practice, it has been found that the cracking time, i.e. effective kinetic residence time, is the time that elapses from the introduction of feedstock into the reaction system until the termination of cracked gas reactions upon quench. The effective kinetic residence time includes the time during which the hydrocarbon and catalyst are in intimate contact and the time from separation until quench. This effective kinetic residence time is from about 0.1 to about 2.0 seconds.

Once separated from the catalyst solids, the effluent, including product gases and unreacted light feed component, is quenched, passes through gas outlet 51 to a second separation zone, zone 3 and into separator 56 along effluent line 59. In the separator 56 of the second separation zone 3, the heavier products leave to further separation along line 95. The lighter components containing the remaining unreacted light feedstock component pass along line 97 to separator 98 where essentially fuel gas components are removed via line 102. The lighter feed and its conjugate olefin move through line 103 to separator 105 where separation takes place and the unreacted light hydrocarbon exits via the recycle outlet 89 into line 90 which returns the light hydrocarbon to the catalytic dehydrogenation system 2, and specifically the acceleration zone 9, for use as acceleration gas.

As stated, use of the recycle as acceleration gas introduced into the acceleration zone 9 with the catalyst solids subjects the recycle component to the harshest catalyst conditions for reaction in the acceleration zone 9, prior to contact with the feedstock in the mix zone 11.

As the effluent leaves the separator 6, the catalyst solids move into the regeneration assembly 8.

Figure 11:
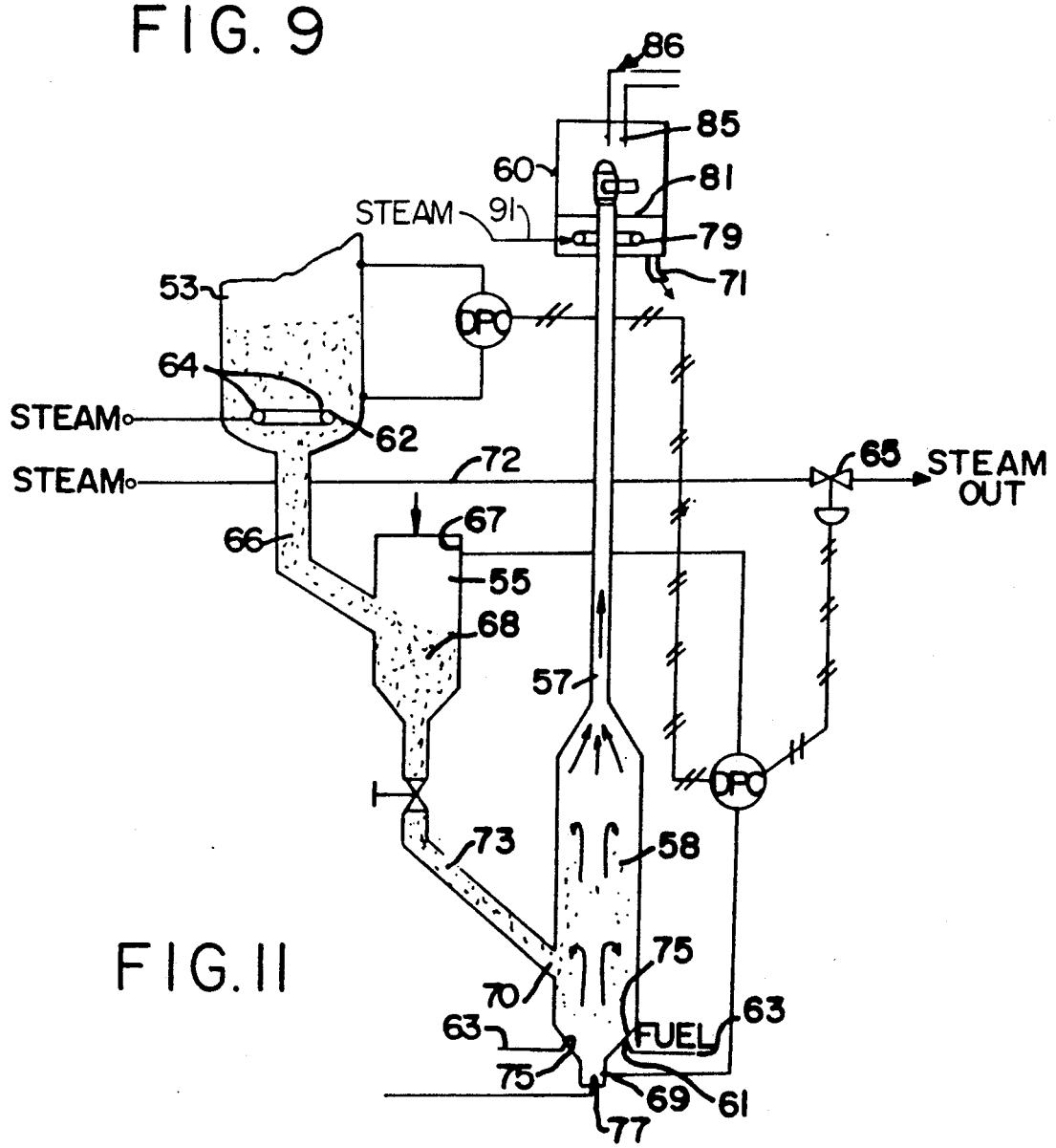
FIG. 11 is a schematic elevational view of the solids regeneration assembly.

As best seen in FIG. 11, the regeneration assembly 8 is comprised of a stripper 53, control hopper 55, entrained bed heater 58, a lift line 57, and a regenerated solids vessel 60.

The stripper 53 is a tubular vessel into which the catalyst solids from the separator 6 are delivered through solids outlet legs extending from the separator solids outlets 38 and from the cyclone diplegs 49. A ring 62, best seen in FIG. 11, having nozzle openings 64, is provided at the bottom of the stripper 53. A stripping gas, typically steam, is delivered to the ring 62 for discharge through the nozzles 64. The stripping gas passes upwardly through the bed of entrained catalyst solids to remove impurities from the surface of the catalyst solids. Approximately, 1.0 to 3.0 pounds of steam at 200° C. to 500° C. temperature and 20 to 200 psig pressure are delivered to the stripper 53 for each 0.5 ton of particulate solids. The stripping steam and entrained impurities pass upwardly through the catalyst solids in the stripper 53 and discharge through a vent line (not shown) to the cracked gas line.

The stripped solids are accumulated in the control hopper 55 for eventual delivery to the entrained bed heater 58. The control hopper 55 is a collection vessel in which solids enter through the standpipe 66 and from which an outlet line 73 extends to deliver solids to the entrained bed heater 58. The assembly of the control hopper 55 and standpipe 66 provides for a slumped bed solids transport system as described in U.S. Pat. Nos. 4,459,071 and 4,453,865, which are incorporated herein by reference. The pressure differential maintained between the slumped bed surface 68 in the control hopper 55 and the exit 70 of the outlet line 73 determines the solids flow rate between the control hopper 55 and the entrained bed heater 58. A line 72 is provided to selectively introduce steam under pressure into the control hopper 55 to regulate the pressure differential. Probes 67 and 69 are placed respectively in the control hopper 55 and entrained bed heater 58 to monitor the pressure differential and regulate the valve 65 in the steam line 72.

The entrained bed heater 58 is essentially tubular in configuration. An array of distinct fuel nozzles 61 fed by fuel lines 63 are arranged essentially symmetrically on the lower inclined surface 75 of the entrained bed heater 58. Air under pressure enters the entrained bed heater 58 through a nozzle 77 arranged to direct the air axially upwardly through the entrained bed heater 58. The air jet 77 provides both the motive force to lift the solids particles upwardly through the entrained bed heater 58 to the regenerated solids vessel 60 and the air necessary for combustion. The fuel is ignited by contact with the hot solids in the presence of air.

The combustion gas/solids mixture moving upwardly through lift line 57 enters the regenerated solids vessel 60 tangentially, preferably perpendicular to the lift line 57, to separate the combustion gases from the solids. As shown in FIG. 3, the vessel 60 has a diptube 85 in the gas outlet nozzle 86 to provide cyclonic movement which improves the separation efficiency of the system.

In operation, the solids slide down the inside edge of the entrained bed heater 58 and are picked up by the central air jet 77 which operates at a velocity of 80 to 150 fps. The superficial velocity in the main body of the entrained bed heater 58 is 8 to 15 fps. The reduction in velocity and the use of a single central jet 77 creates a circulation in dilute phase within the expanded portion of the bed. The entrained solids fall to the side and are re-entrained in the jet 77.

The velocities are such that there is a net transport of solids up the lift line 57 with the wide spot in the line creating a zone of recirculation and hence higher solid density and residence time. Practice shows that the solids on the average recirculate about 10 to 15 times compared to the net throughput. The characteristics and advantages of the entrained bed heater 58 include a recirculation system that creates a higher solids density that minimizes peak temperature which could damage catalyst solids. In addition, the combustion in the entrained bed heater 58 occurs in the gas phase. The solids are suspended in the gas and thus the combustion is rapid and the gas and fuel are intimately mixed in the combustion zone of the bed heater 58.

The combustion reaction in the entrained bed heater 58 includes the coke coating the particulate solids. Thus, the feed to air ratio is maintained for a nominal 10% excess of air over fuel and insures that all the coke on the catalyst solids is burned and contributes to the solids heating process. The reaction is of a type similar to $CH_x + O_2 \rightarrow H_2O + CO_2$.

The regenerated solids vessel 60 is a cylindrical vessel provided with a standpipe 71, seen in FIG. 4, extending to the reactor hopper 31. The structure of the regenerated solids vessel 60, shown in FIG. 11, provides for a stripping zone 81 which is fluidized by the introduction of stripping steam via line 91 into stripping ring 79. Following stripping, solids flow into slumped bed standpipe 71 for entry into control hopper 31. The pressure in the vapor space in control hopper 31 is used to control the flow of solids into the acceleration zone 9.

The solids flow from the rectangular orifices or solids inlet passages 19 is what can be described as extrusion flow. The solids are in dense phase until picked up by the acceleration gas. A pressure drop of 0.5 to 5.0 psi is used to control the rate of solids flow to the reactor mixing section 11.

The process of the invention proceeds by delivering acceleration gas such as steam through line 27 or, preferably, recycled, unreacted light feed component through line 90 at a temperature of from about 60° F. to about 600° F. through the acceleration gas nozzles 29 into the acceleration zone 9. The solids mixture then passes into the mix zone 11, through rectangular orifices 25 at a temperature of from about 1300° F. to about 1800° F., where mixed hydrocarbon feedstock at a temperature of from about 60° F. to about 1000° F. is delivered through the feed nozzles 28. The mixed hydrocarbon feedstock mixes with the hot catalyst solids and is reacted at a temperature of from about 900° F. to about 1500° F. in the elongated reaction section 12. The pressure in the reactor is from about 10 to about 100 psi and the residence time or contact time from the hydrocarbon feed entry to the effluent quench is from about 0.1 to about 2.0 seconds.

The reacted gases and unreacted light feed component are separated from the spent catalyst solids and are then quenched by direct contact with quench fluid to lower the temperature to below 1100° F. and preferably below 1000° F. Thereafter, additional cooling is performed to reduce the cracked effluent temperature to that required for fractionation.

The catalyst solids are stripped of residual hydrocarbons in the stripper 53 by steam at temperatures of from about 1100° F. to about 1500° F. with any unstripped hydrocarbons being consumed as fuel in the bed heater 58. The stripped catalyst solids are then delivered to the entrained bed heater 58 at a temperature of from about 1100° F. to about 1500° F. Fuel having a BTU content of 17,000-22,000 BTU/LB and 12 to 17 pounds of air per pound of fuel and coke are continuously fed to the entrained bed heater 58 and combusted with the coke (carbon) on the catalyst solids at temperatures of 1200° F. to 1700° F. and a pressure of 6 to 60 psi. Hot catalyst solids are delivered to the regenerated solids vessel 60 at a temperature of 1200° F. to 1700° F. where the combustion gases are separated in cyclones 50 and exhausted as flue gas. The flue gas has no BTU content and is used to indirectly preheat feedstock or generate steam.

The hot solids are returned to the reactor 4 through the reactor hopper 31 and rectangular orifices 19 at a temperature of from about 1300° F. to about 1800° F.

The QC system of the present invention increases the amount of exposed catalyst surface area available for reaction, compared to fixed bed dehydrogenation systems, by allowing for the utilization of smaller catalyst particles. The QC system of the present invention is capable of using fluidizable catalyst solids with an average particle size ranging from about 20 microns to about 500 microns, and a surface area in the range of 20 m²/g to approximately 450m²/g. The smaller catalysts have more external surface and reduced diffusional resistance (shorter pores) than larger particles. Both of these characteristics are favored for short residence time reactions.

The QC system of the present invention also overcomes the inherent limitations of current reactor technology arising from relatively large pressure drops. Reaction to olefins is favored by low pressure. The present invention is capable of achieving essentially plug flow reaction conditions with essentially no pressure drop in the reactor zone. Therefore, the reaction can be run at short time, high heat input and small solids with low $\Delta P$, unobtainable with fixed beds.

The present invention also allows enhanced temperature profile control within the reaction zone. This is achieved by independently controlling the incoming temperature and/or flow of the catalyst particles.

The reactor velocity is determined from the volume flow of the reacting mixture (mass flow, MW, P, T) and the diameter of the reactor. The velocity is limited by certain system erosion criteria and other mechanical considerations. It is known in mixing and separation processes that the length to diameter ratio (L/D) is critical. The total residence time in the system is a function of the velocity as defined above and the length of the zone. For any desired residence time, the velocity-length relationship is set. The L/D ratio then sets the diameter with the specified length. The capacity of the present reactor is set by velocity criteria and the total cross-sectional area. Residence times in the order of 200 milliseconds can be achieved at capacities equivalent to other commercial dehydrogenation processes. For example, a single reactor module can process the equivalent of 130 MM lb/yr propylene from propane. Residence times greater than 200 milliseconds are possible by simply lengthening the reactor section (with the mixing and separation zones intact) or reducing the throughput. Residence times less than 200 milliseconds are possible by reducing the capacity of a given module (reducing) length and thus diameter at constant velocity).

The present invention is particularly well adapted for use in a low residence time fluidized solids cracking apparatus, such as those described in U.S. Pat. Nos. 4,814,067 and 4,919,898 to Gartside et al., which are both incorporated herein by reference.

The term "catalytic activity", as used in this application, refers to the rate of reaction occurring in the presence of a catalyst compared to the rate of the same reaction occurring without the catalyst. It is a relative term that must be defined with reference not only to the specific reaction (e.g., dehydrogenation) but to a number of other parameters including the catalytically active ingredients, their specific form (e.g., crystalline structure), the presence or absence of any promoters, the amount of catalyst present, the carrier, its structure (e.g., pore size, surface area, etc.), and the operating conditions including not only temperature and pressure, but also other reactants, diluents, or "poisons". There are, for example, cracking catalysts, reforming catalysts, synthesis catalysts, as well as dehydrogenation catalysts; all named by their ability to promote (increase the rate of) a specific chemical reaction. In many references, however, catalytic activity is used synonymously with reaction rate and definitions are thus even more critical.

The terms "high activity" and "low activity" are also relative and must be defined against a reference, defined herein as the "commercial" catalyst.

As set forth above, the present process contemplates the use of catalysts with increased activity when compared with the "commercial" catalyst. Catalyst activity is generally defined as the rate of reaction based upon similar operating conditions. The "commercial" catalyst employs a model based kinetic expression of $k = Ae^{-E/Rt}$ where $A = 0.389$ gmol/sec-m² catalyst area and E (activation energy) = 26,052 cal/gmol using a catalyst having 16.8% $Cr_2O_3$ having a surface area of 250 m²/gm with 2% potassium oxide promoter on a support of alumina ($Al_2O_{23}$) reduced with dry hydrogen. (See, Ashmawy, *Kinetic Investigations of the Reaction of Propane with Sulfer-Dioxide on a Palladium-Alumina Catalyst*, J. Chem. Tech. Biotechnol., 1984, Vol. 34A, pp. 183-6). Under the conditions of commercial operation, typically 500° C., the calculated rate is $0.16 \times 10^{-7}$ gmol/sec-m². Therefore, the difference in catalyst activities will be viewed based on a "commercial" catalyst with an activity value of 1.0 for comparison.

In the present invention, catalysts having increased activity are favored due to the short residence time (period when the catalyst and feedstock are in contact) of the reaction. Although catalysts having activities of 1 or greater are acceptable, catalyst activity of about 50 to 300 (considered moderate) and activities of over 300 (considered high) are preferred for the present dehydrogenation process.

It is known in the art that catalyst activity in a system can be increased through the use of more active catalysts, crystalline or preferred catalyst structures, certain pretreatments, increasing the metal loading, increasing in the catalyst surface area, use of certain promoters, etc. For example, use of a Pd catalyst having a surface area of 250 m$^2$/gm, without a promoter, with low active metal loading and an unknown reduction method has a reaction rate 1.44 times greater than the "commercial" catalyst. Further, increasing the metal content from 10% to 16.8% increases the rate 1.67 times, adding a promoter increases the rate by 1.6 times, increasing the surface area to 450 m$^2$/g increases the rate 1.8 times and changing the reduction method to a dry hydrogen method increases the rate by an additional 1.9 times. Using variations consistent with these examples, catalysts can be increased to over 1,000 and indeed over 10,000.

Catalysts of moderate and high activity, appropriate for the practice of the present invention, can thus be prepared by one skilled in the art.

A preferred catalyst for practice of the present invention is a palladium-alumina catalyst with a surface area of 450 m$^2$/gm obtained by loading the alumina support with 15 wt % of Pd, pretreating with a dry hydrogen reduction method, adding a sulfer dioxide promoter. The activity of this catalyst is about 142.

The process of the subject invention is directed to processes operating at short kinetic residence times and high temperatures. This allows operation in more favorable equilibrium conditions without the excessive thermal degradation that would occur if higher temperatures were used with conventional kinetic residence times. The process operates with a dilute flowing catalyst system where the catalyst density is considerably less than that of a packed or fixed bed. The amount of catalyst is thus a function of the catalyst to feed ratio (a variable), however, the catalyst to feed ratio is generally contemplated to be between about 5:1 to 100:1.

Commercial fixed bed dehydrogenation reaction systems operate at temperatures that average near 650° C. Further, in a fixed bed, the catalyst is in a packed form at its maximum density with respect to the gas (maximum sq. meters of catalyst surface per unit volume). Since the rate of reaction is a function of both the activity of the catalyst and of the quantity of catalyst present, the process of the subject invention preferably employs a higher catalyst activity than that for a fixed bed, all else being equal, to produce an equivalent yield.

This is best demonstrated by example. At a temperature of 650° C. and the solid density of a packed bed, the ratio of the rate of catalytic dehydrogenation to the summation of the rates of the rate of thermal dehydrogenation and thermal cracking of propane is 3.0. In other words, in commercial dehydrogenation systems operating under their preferred conditions, the rate of catalytic reaction is 3 times the rate of thermal reaction. This ratio produces high yield selectively. This same ratio is achieved for the subject process operated at the same temperature (650° C.) and its normal process solid flow (lower density) when the rate constant for catalytic dehydrogenation is approximately 20 times greater than presented above. The higher rate of catalytic reaction is required to compensate for the lower catalyst density.

As the temperature is increased to achieve a more favorable equilibrium, the rates of the thermal reactions increase more rapidly than do the rates of the catalytic reactions. For the fixed bed at a temperature of 750° C. using commercial catalysts, the thermal reactions predominate and the rate of catalytic dehydrogenation is 60% of the sum of the rates of the thermal reactions. At this temperature level, the rate constant for the catalytic dehydrogenation reaction to be used in the subject process must be 100 times larger than that for the commercial fixed bed catalyst (also at 750° C.) to achieve the current commercial ratio of catalytic rate to thermal rate (i.e , a ratio of 3.0)

For the purpose of this application, a catalyst is considered to have a "high activity" if the catalytic dehydrogenation rate constant is greater than a factor of 300 higher than that of the "commercial" catalyst at the same temperature. A catalyst is considered to have a "moderate" activity if the catalytic dehydrogenation rate constant is between a factor of 50 and 300 higher than that of the "commercial catalyst" at the same temperature. Thus, operation of the process of the invention with high activity catalyst at its lower catalyst densities will result in a higher ratio of catalytic to thermal reactions than existing commercial systems when operated at conventional temperatures (i.e., approximately 650° C). Further, it will result in a similar ratio (3.0) at very high temperatures (above 750° C.). Operation of the process with a moderate activity catalyst will give high catalytic to thermal reaction rate ratios at conventional temperatures (650° C.) and similar ratios at higher temperatures (750° C.). Operation of the process with conventional catalyst provides improvements in low feed dilution levels, low pressure drop and facilitates catalyst regeneration and reacted product gas quenching.

EXAMPLES

In order to evaluate the differences between the present dehydrogenation process and the coil/fixed bed process, two different feed mixtures of propane and ethane were assumed and each system was theoretically tested.

Initially, as explained above, two options are available to the practitioner depending on the products desired. If thermal products are desired, the feeds are cracked in a coil either together or separately to maximize the production of ethylene from the propane/ethane mixture. A plant designed for such a process would have limited recycle capability unless a number of standby extra furnaces are included wherein the conversion from ethane to ethylene is generally high. This is important when considering the concentration of ethane in the feed because a plant designed for a low fresh feed ethane flow (hence low recycle) cannot handle higher concentrations of ethane in the feedstock without cutting back on total mass flow to allow for higher recycle.

If, however, catalyst yields are desired from the coil/fixed bed system, two separate trains of processing are required. First, the paraffins of the mixed feed must be separated into the two trains, the paraffins processed separately and then the effluents combined. Ethane cannot be processed on a fixed bed since conversions are on the order of 20% and thus would result in very high recycle rates requiring substantial separation system energy and capacity.

For propane/ethane mixtures, a combination of cracking coils and fixed bed dehydrogenation units are required. For mixtures of paraffins with a higher carbon number, separate dehydrogenation units would be required since operation of a mixture would lead to excessive fouling or underconversion as previously discussed. Also, once a commitment is made to dehydrogenation in a coil/fixed bed system there is no option for thermal cracking.

The current system, however, contemplates thermal cracking or catalytic dehydrogenation in the same unit, and in some cases a mixture of the two. The QC reactor system is unique in that the recycle flow of the more refractory, lighter feed can be utilized as the acceleration gas and therefore can be processed in the acceleration zone 9 where significantly more severe conditions can be attained. The acceleration gas sees the highest temperatures and much higher solids to hydrocarbon flows, since solid flow is set by the entire feed flow heat and catalytic requirements. The design of the acceleration zone 9 is such that residence times of 50-100 milliseconds are achieved prior to the introduction of the main feedstock, in a staged approach. During this time, significant conversion of the recycled unreacted light component feedstock can be achieved.

In operating from thermal yields to catalytic yields, the only difference in the QC cases is the use of fluidized catalyst solids compared to an inert solid (for thermal cases) and the operating temperatures of the system. A wide range of processing options can be handled in a single unit without encountering limitations in capacity created by varying recycles, etc. This will be clear when specific examples are discussed below.

The following examples utilize as a basis for the calculations a fresh feed flow of 20 MT/hr consisting of a 50/50 weight mix of ethane and propane in one case and a 20/80 mix of ethane and propane in the other case. Table 3 summarizing the information set forth in FIGS. 13A-E and 14A-F follows.

THE 50/50 PROPANE/ETHANE CASE

Figure 13A:
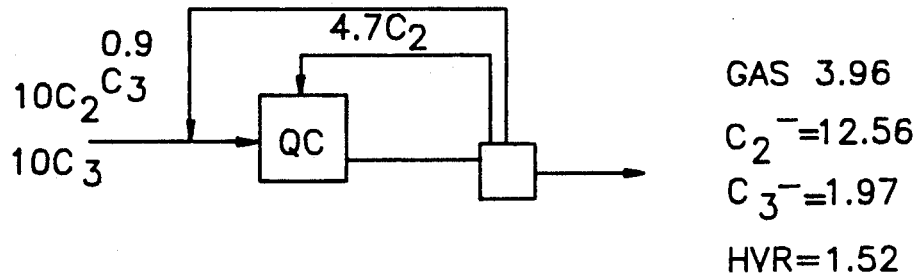
FIG. 13A is a flow chart of the thermal products from a 50/50 propane/ethane feed in a QC reactor using an inert solid.

If thermal products are desired, the 50/50 propane/ethane mix (10 MT/hr each) can be co-cracked in a coil or in a QC system. The 50/50 QC thermal case using inert solids is shown in FIG. 13A. The 50/50 coil case is shown in FIG. 13D.

The QC case uses a high conversion acceleration zone thermal cracking of the recycle ethane (4.7 MT/hr), the ethane used as an acceleration gas, to limit the overall unit traffic and thus save capital cost and energy. The conversion in this zone is 86% versus the 60–70% range commonly employed by a coil due to furnace limitations. The higher conversion recycle thermal cracking has a slightly lower overall selectivity (ethylene loss from 12.92 to 12.56 MT/hr product) which is offset by the 7.5% reduction in hydrocarbon flow total traffic due to low recycle at the higher conversion (25.6 MT/hr in FIG. 13A as opposed to 27.7 MT/hr in FIG. 13D).

Figure 13B:
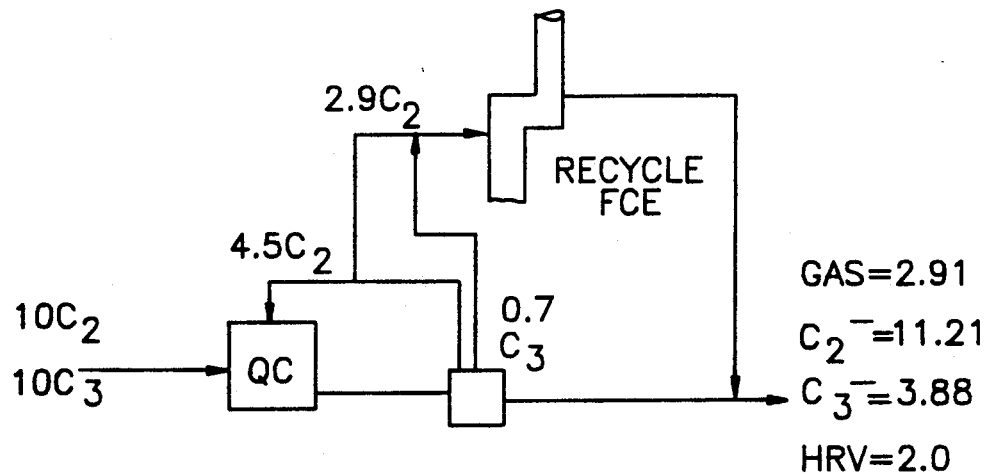
FIG. 13B is a flow chart of the thermal/catalytic products from a 50/50 propane/ethane feed in a QC reactor having catalyst activity of about 100.
Figure 13C:
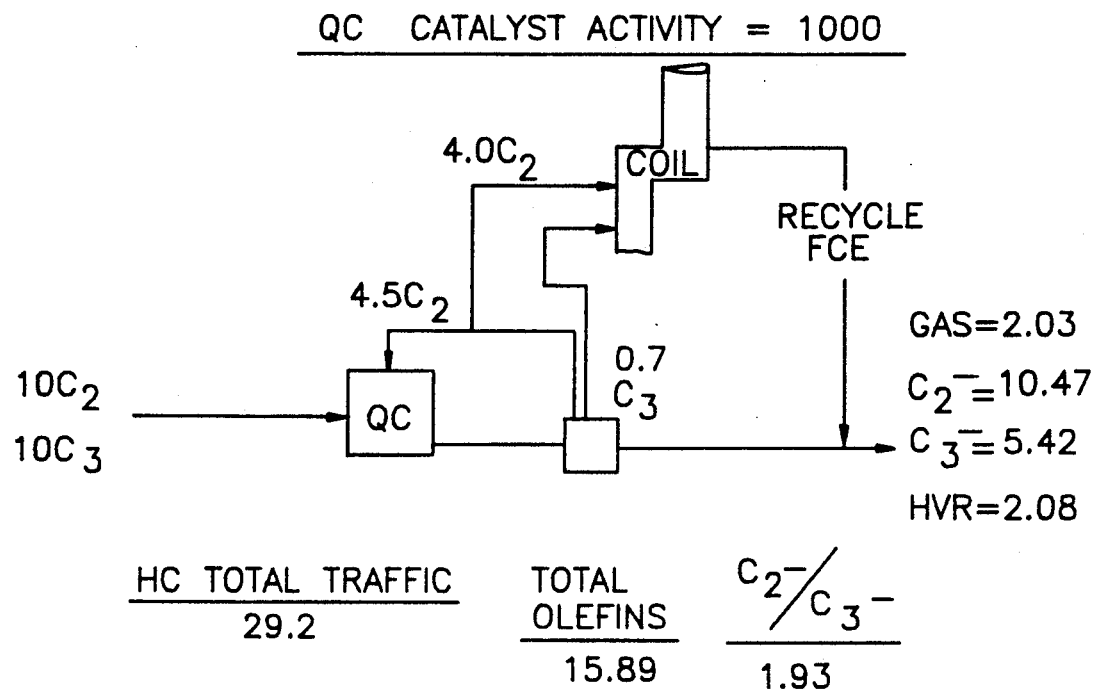
FIG. 13C is a flow chart of the thermal/catalytic products from a 50/50 propane/ethane feed in a QC reactor having catalyst activity of about 1000.
Figure 13D:
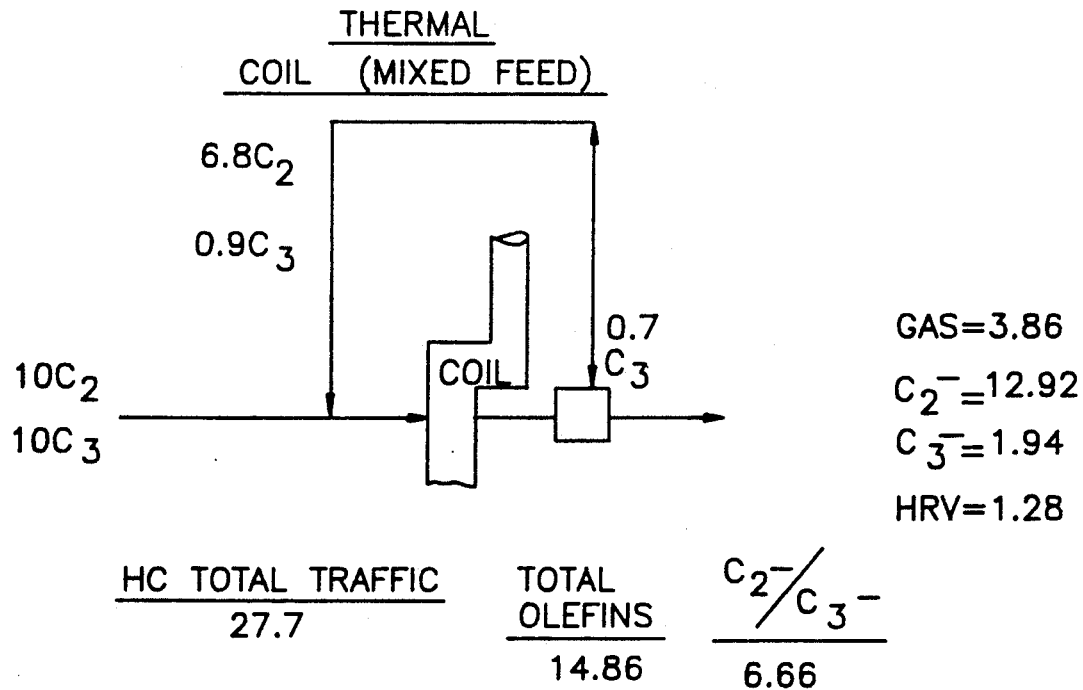
FIG. 13D is a flow chart of the thermal products from a 50/50 propane/ethane feed in a coil process.

FIGS. 13B and 13C show two catalytic QC cases using two different catalyst activity levels. The increased catalyst activity results in increased catalytic control of the yield spectrum. For both of these cases, a separate small recycle furnace to co-crack the excess ethane/propane mixture is used. This furnace is required only because of the limitations of capacity of a single QC and the choice of a total of 20 MT/hr fresh feed. The acceleration zone 9 can handle approximately 4.5 MT/hr of a feed while the total flow is on the order of 25 MT/hr.

Figure 13E:
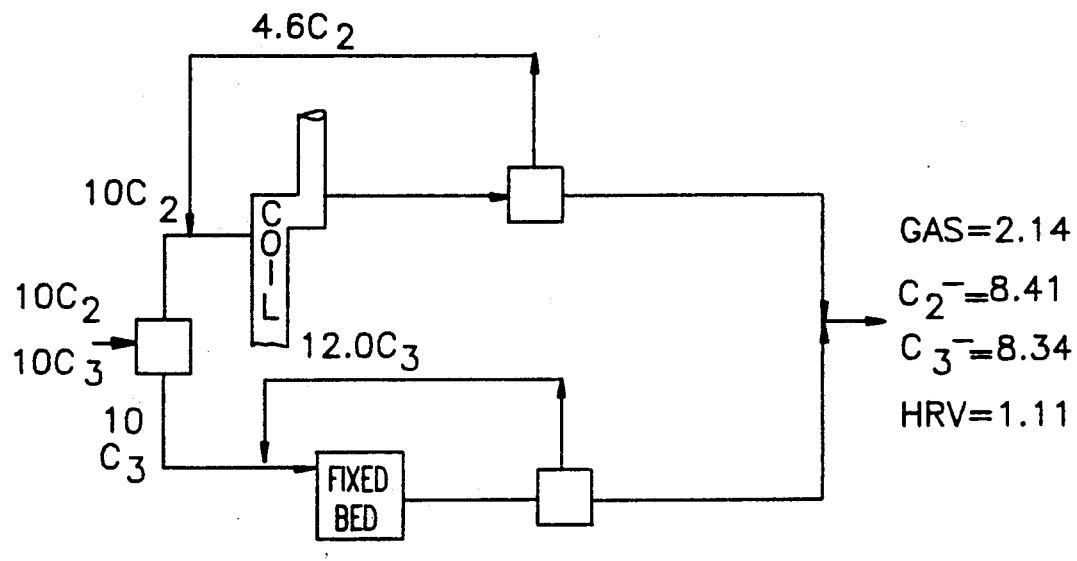
FIG. 13E is a flow chart of the thermal/catalytic products from a 50/50 propane/ethane feed in a process where ethane is cracked in a coil and propane dehydrogenated in a fixed bed.

At the other end of the spectrum is the coil/fixed bed case shown in FIG. 13E. The 50/50 mix is separated with the ethane cracked in a coil and the propane processed in a dehydrogenation unit. Very high hydrocarbon traffic results from the high recycles in the fixed bed dehydrogenation case. In fact there are three separation zones instead of one.

In comparing the catalytic option (conventional vs QC), the differences in yield patterns and overall plant traffic standout. The coil-fixed bed system (FIG. 13E) has significantly more traffic (hence capital cost) than the QC system (36.6 MT/hr as opposed to 28.1 or 29.2 MT/hr). However, due to the higher selectivity achieved through feedstock separation, the total olefins are higher (16.75 MT/hr versus either 15.09 or 15.89 MT/hr for the QC cases). The differences are that in the QC, some of the heavier feed (propane) goes to fuel components at the higher conversions.

Also, the QC is able to achieve a variation in yield structure by varying catalyst activity. Conventional processing is limited to an ethylene/propylene ratio of either 6.66 (thermal) or 1.01 (catalytic). Intermediate ratios are not possible. The QC system on the other hand can achieve the thermal ratio of 6.38 or other ratios down to 1.93 from the mixture directly by varying catalyst.

Comparisons to coil capacity have been discussed, however, simply put, a single coil has a small capacity (approximately 0.5 to 1 MT/hr) thus the size of a coil cracker can vary with the number of coils installed in a single furnace or multiples of furnaces with a fixed number of coils each. The QC yield pattern can vary significantly from a C2-/C3- ratio of 6.4 (thermal) to 1.9 (catalytic) in a single unit with only marginal change in hydrocarbon traffic.

There are two other points of note. First, QC is not limited by catalyst fouling since the catalyst is regenerated continuously. This is especially important when processing heavier paraffins where high conversions lead to coke which fouls the catalyst.

Second, the yields developed for the QC catalyst cases assume no dilution. The feedstock entering to the acceleration zone is "neat" and is then used to dilute the main feed flow. On the other hand, dilution is required in a coil system to keep tube fouling under control. Typically 0.2 to 0.3 wt/wt ratios of diluent are required with the coil system which consumes reactor and separation system capacity. For the fixed bed cases, typically 1–1.25 wt/wt ratio is used to both control fouling and provide heat for the reaction. This increases plant traffic considerably above the numbers shown in FIGS. 13D and 13E.

THE 80/20 PROPANE/ETHANE CASE

Figure 14A:
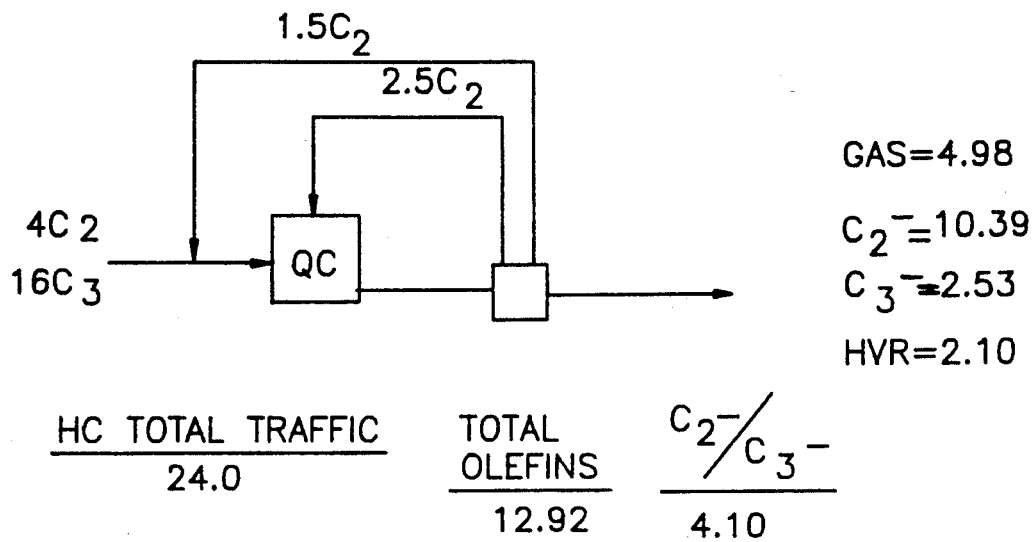
FIG. 14A is a flow chart of the thermal products from an 80/20 propane/ethane feed in a QC reactor.
Figure 14B:
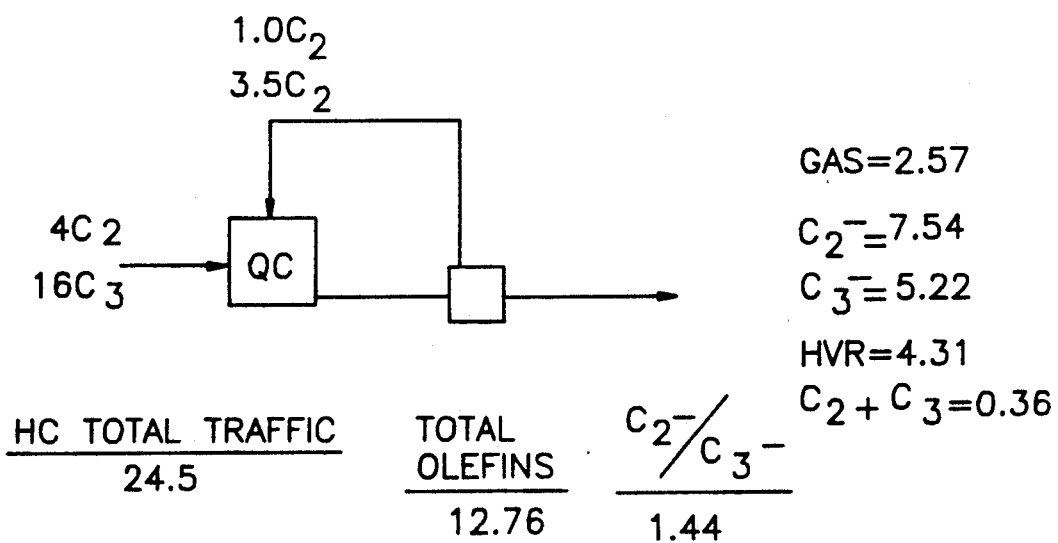
FIG. 14B is a flow chart of the thermal/catalytic products from an 80/20 propane/ethane feed in a QC reactor having catalyst activity of about 100.
Figure 14C:
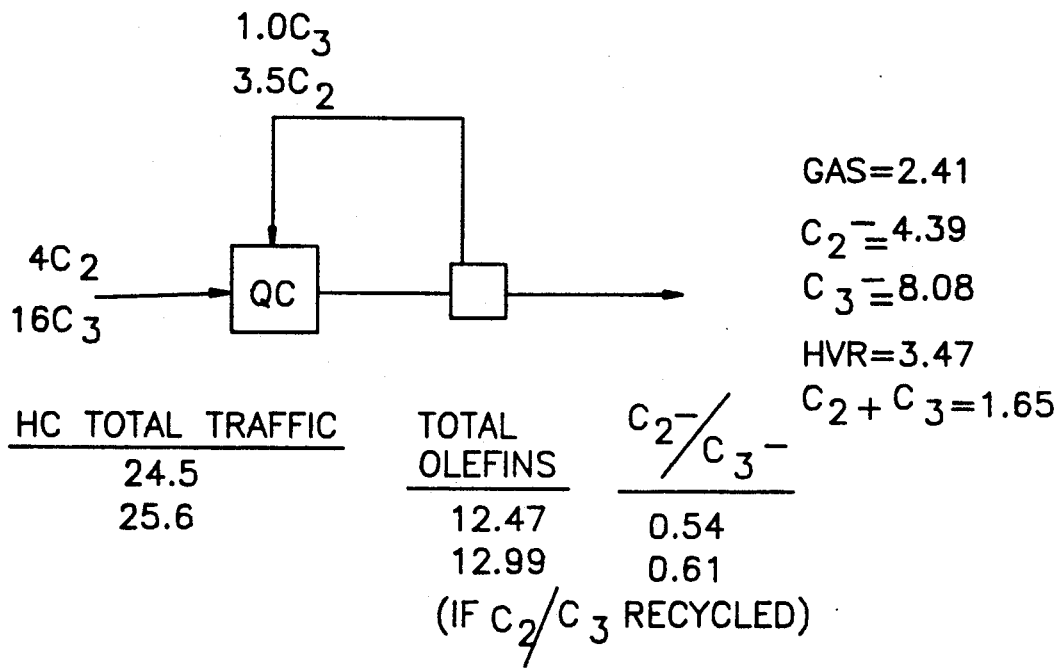
FIG. 14C is a flow chart of the thermal/catalytic products from an 80/20 propane/ethane feed in a QC reactor having catalyst activity of about 1000.
Figure 14D:
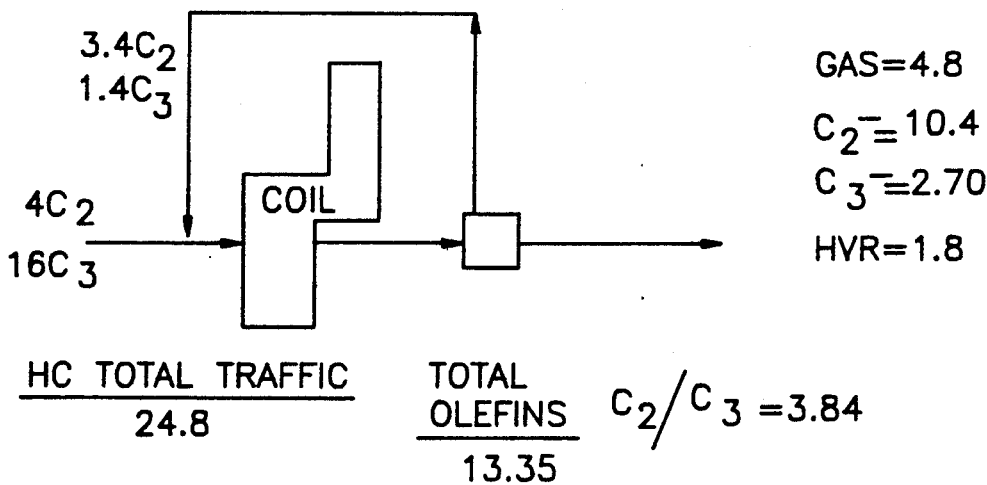
FIG. 14D is a flow chart of the thermal products from an 80/20 propane/ethane feed in a coil bed process.
Figure 14E:
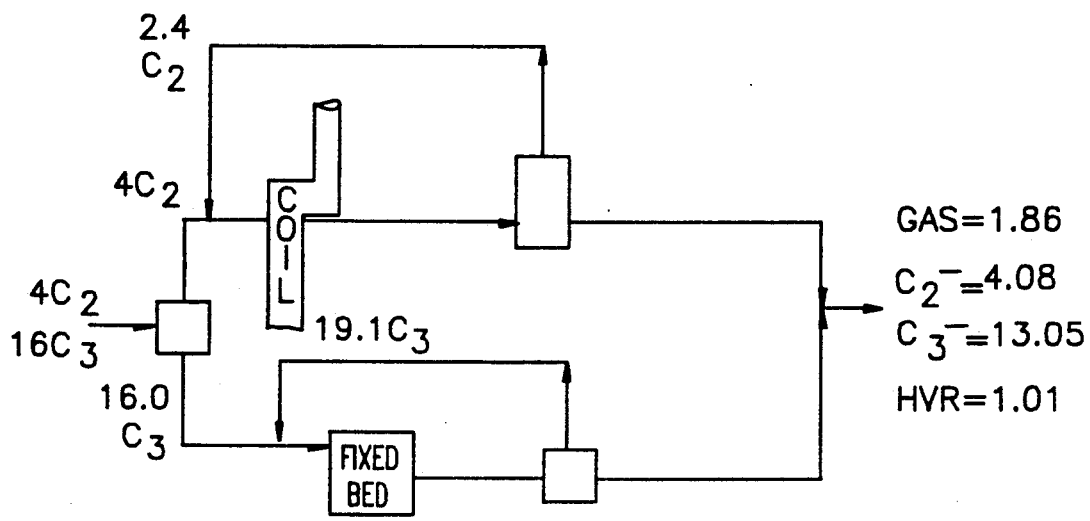
FIG. 14E is a flow chart of the thermal/catalytic products from an 80/20 propane/ethane feed in a process where ethane is cracked in a coil and propane is dehydrogenated in a fixed bed.
Figure 14F:
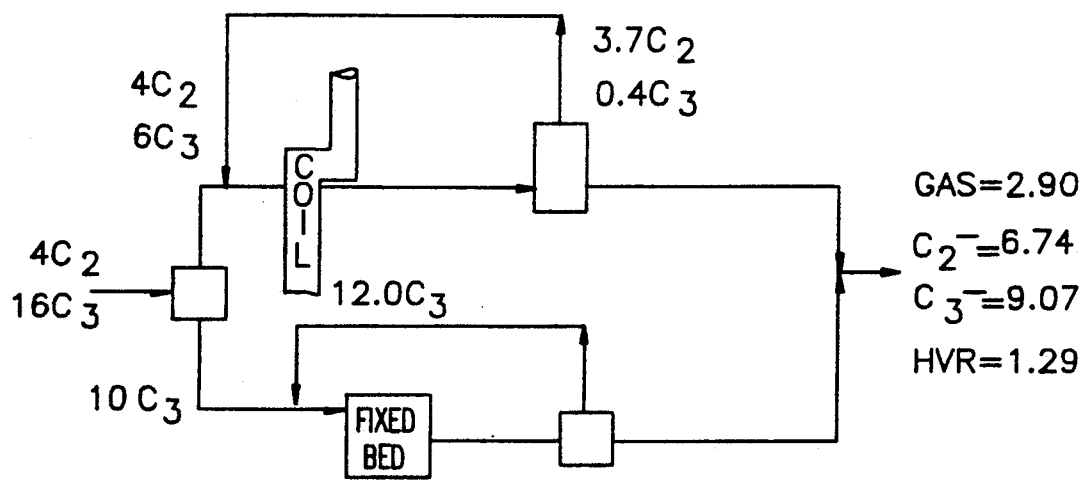
FIG. 14F is a flow chart of the catalytic products from an 80/20 propane/ethane feed in a process where ethane is cracked in a coil and propane dehydrogenated in a fixed bed, the fixed bed capacity set by the 50/50 case.

The 80/20 QC case is shown thermally in FIG. 14A and catalytically in FIGS. 14B and 14C with varying catalyst activity. The 80/20 coil-fixed bed case is shown thermally in FIG. 14D and catalytically in FIG. 14E. FIG. 14F shows a catalytic fixed bed plus coil reaction where the fixed bed capacity is limited to the 50/50 flow case.

The higher concentration of the heavier feed has the following effect on the comparison.

The QC case using inert solids (thermal) will be considered first. Processing the 80/20 mixture can be easily achieved (total plant throughput actually decreases from 25.6 MT/hr shown in FIG. 13A to 24 MT/hr shown in FIG. 14A). For the coil cracking case, the same is true. Required throughput drops from 27.7 to 24.8 MT/hr (compare FIGS. 13D and 14D). Both QC thermal and coil thermal product yields are similar (ethylene/propylene ratios of 4.1 and 3.84 respectively).

When catalytic processing is desired, major limitations are encountered for the coil-fixed bed case. Since propane is catalytically dehydrogenated with high recycle in the fixed bed case, increasing the heavy component increases plant traffic from 36.6 MT/hr (FIG. 13E) to 41.5 MT/hr (FIG. 14E). If normal diluent flows from the coil and fixed bed systems are considered, the actual traffic increases from 67.8 MT/hr to 87 MT/hr, or by 28 percent. In most designs, this is not possible without modifications. More specifically, if one designs, this is not possible examines the propane dehydrogenation portion alone, its capacity would have to increase from 22 MT/hr to 35.1 MT/hr, or almost 60 percent.

The QC case, however, can process the mixture without any change in unit capacity. As can be seen from FIGS. 14B and 14C, plant traffic remains essentially constant at approximately 25 MT/hr and below the 50/50 case requirement of 25.6 MT/hr. Full feedstock flexibility is maintained without any requirement for added capacity.

FIG. 14F shows the conventional processing with the size of the propane dehydrogenation unit fixed at the capacity of the 50/50 case. In this case, the balance of the propane is fed to a coil pyrolysis unit. The coil pyrolysis will handle this flow since it had an installed capacity of 14.6 MT/hr (FIG. 13E). Note, however, the shift in ethylene/propylene ratio from 0.31 for the specifically designed case (FIG. 14E) to 0.74 (FIG. 14F).

Some brief words on other paraffin pairs are also in order. The compatibility of coprocessing in a fixed bed catalytic mode is related to the differences in reaction rates. As shown on Table 1, the C2/C3 system is the most incompatible. However, even C4 mixtures show a significant difference in reactivity that will lead to high recycles of the less reactive component. Importantly, fouling increases with molecular weight and the differences become more important as severity limits become more strict to avoid fouling in fixed beds.

QC overcomes the problems of processing mixtures of paraffins by exploiting four parameters of the system:
a. the ability to operate without fouling limitations;
b. the ability to operate at higher temperatures; and shorter times to get high conversion for both paraffins without excessive thermal degradation;
c. the ability to operate with either catalyst solids or inert solids to avoid widely varying recycle requirements and thus reduce separation capacity and energy; and
d. the ability to recycle the less reactive paraffin to an acceleration zone where more severe processing conditions exist without requiring a separate unit.

We claim:

1. A process for the dehydrogenation of a mixture of light paraffins of five (5) or fewer carbons comprising:
   (a) introducing hot, fresh catalytic solids into an acceleration zone and accelerating the solid with an acceleration gas comprising an unreacted, recycled lower number paraffin component;
   (b) passing the accelerated catalytic solids from the acceleration zone into a mixing zone;
   (c) introducing a mixed paraffin feedstock comprising a higher number paraffin component and a lower number paraffin component into the mixing zone, and into contact with the accelerated catalytic solids;
   (d) passing the feedstock/catalyst mixture out of the mixing zone and into a reaction zone where the higher number paraffin is substantially completely converted to its corresponding olefin and the lower number paraffin is partially converted to its corresponding olefin in a hydrocarbon effluent;
   (e) passing the hydrocarbon effluent/catalyst solids mixture into a separation zone;
   (f) separating the catalyst solids from the hydrocarbon effluent gas in the separation zone;

TABLE 3

| Figure | Case | C2H4 MT/hr | C3H6 MT/hr | C2−/C3− wt/wt | Total Olefins MT/hr | Total HC Traffic MT/hr |
|---|---|---|---|---|---|---|
| | 50/50 Propane/Ethane Processing Total Feed 20 MT/hr Fresh Feed | | | | | |
| 13 A | QC Thermal | 12.6 | 2.0 | 6.3 | 14.5 | 25.6 |
| 13 B | QC Cat = 100 | 11.2 | 3.9 | 2.9 | 15.1 | 28.1 |
| 13 C | QC Cat = 1000 | 10.5 | 5.4 | 1.9 | 15.9 | 29.2 |
| 13 D | Coil Thermal | 12.9 | 1.9 | 6.7 | 14.9 | 27.7 |
| 13 E | Coil Plus Fix Bed Dehydro | 8.4 | 8.3 | 1.0 | 16.8 | 36.6 |
| | 80/20 Propane/Ethane Processing Total Feed 20 MT/hr Fresh Feed | | | | | |
| 14 A | QC Thermal | 10.4 | 2.5 | 4.1 | 12.9 | 24.0 |
| 14 B | QC Cat = 100 | 7.5 | 5.2 | 1.4 | 12.8 | 24.5* |
| 14 C | QC Cat = 1000 | 4.4 | 8.1 | 0.5 | 13.0 | 25.6* |
| 14 D | Coil Thermal | 10.4 | 2.7 | 3.8 | 13.4 | 24.8 |
| 14 E | Coil Plus Fix Bed Dehydro | 4.1 | 13.1 | 0.3 | 17.1 | 41.5 |
| 14 F | Coil Plus Fix | 6.7 | 9.1 | 0.7 | 15.8 | 36.1** |

*No recycle furnace included (acceleration zone at maximum)
**Sized to have same overall capacity as case 13 E For the QC system, the recycle quantities are low and the economics of a recycle furnace must be considered. Note, however, that the two major differences between the present invention and current technology still exist. If a plant is designed using coil crackers for thermal yields or with fixed beds and coils for catalytic yields, there is limited product slate flexibility to go to the other. This is not true for the present system.

(g) quenching the hydrocarbon effluent once it leaves the separation zone;
(h) separating the unreacted lower number paraffin component of the hydrocarbon effluent from the hydrocarbon effluent; and
(i) recycling at least a portion of the unreacted lower number paraffin component to the acceleration zone for use as at least a portion of the acceleration gas of step (a) to accelerate the catalytic solids wherein the unreacted lower number paraffin component first contacts the fresh, hot catalyst to allow for dehydrogenation and thermal cracking to a greater degree than the mixed paraffin feedstock thereby resulting in substantially complete dehydrogenation of each of the light paraffins.

2. The process of claim 1 wherein the mixed paraffin feedstock is preheated to a temperature of from about 60° F. to about 600° F.

3. The process of claim 1 wherein the catalyst solids have an activity of greater than about 5.

4. The process of claim 3 wherein the catalyst solids are selected from the group consisting of a metal from the noble metal group, a metal from the transition metal group, a metal oxide from the noble metal group, a metal oxide from the transition metal group, an alkali compound, a tin oxide, a lead oxide, and combinations of the foregoing.

5. The process of claim 4 wherein the catalyst solids comprise particles of from about 20 to about 500 microns in diameter and have a surface area of from about 20 to about 450 $m^2/g$.

6. The process of claim 4 wherein the weight ratio of catalyst of feedstock in the feedstock/catalyst mixture of part (d) is from about 5:1 to about 100:1.

7. The process of claim 1 further comprising regeneration of the catalyst solids separated from the product gas and recycle of the regenerated catalyst to the acceleration zone.

8. The process of claim 1 wherein the catalyst solids are preheated prior to introduction into the acceleration zone to a temperature in the range of from about 1300° F. to about 1800° F.

9. The process of claim 1 wherein the recycled, unreacted lower number paraffin component is mixed with the catalyst for acceleration and the mixture moves through the acceleration zone and into the mixing zone in less than 0.25 seconds.

10. The process of claim 9 wherein the recycled, unreacted lower number paraffin component is introduced to the catalyst for acceleration and the mixture moves into the mixing zone in about 0.05 to about 0.15 seconds.

11. The process of claim 10 wherein the feedstock/catalyst solids passes from the mixing zone into the reaction zone at about 50 ft/sec.

12. The process of claim 1 wherein the reaction conditions include a kinetic residence time, from when the feedstock is contacted with the catalyst solids to when the hydrocarbon effluent is quenched, of from about 0.1 to about 2.0 seconds.

13. The process of claim 8 wherein the temperature in the reaction zone is from about 900° F. to about 1600° F.

14. The process of claim 9 wherein the reaction zone is maintained at a pressure of from about 10 psig to about 100 psig.

15. The process of claim 1 wherein there is no input of heat by indirect means.

16. A process fir the dehydrogenation of a mixture of light paraffins of five (5) or fewer carbons comprising:
(a) introducing fresh catalytic solids at a temperature of from about 1300° F. to about 1800° F. into an acceleration zone and accelerating the solids with an acceleration gas comprising an unreacted, recycled lower number paraffin component;
(b) passing the accelerated catalytic solids from the acceleration zone into a mixing zone at a speed of from about 5 fps to about 150 fps;
(c) introducing a mixed paraffin feedstock comprising a higher number paraffin component and a lower number paraffin component preheated to a temperature of from about 60° F. to about 600° F. into the mixing zone and into contact with the accelerated catalytic solids;
(d) passing the feedstock/catalyst mixture out of the mixing zone and into a reaction zone where the higher number paraffin is substantially completely converted to its corresponding olefin and the lower number paraffin is partially converted to its corresponding olefin in a hydrocarbon effluent/spent catalytic solids mixture;
(e) passing the hydrocarbon effluent/spent catalytic solids mixture into a separation zone;
(f) separating the spent catalytic solids from the hydrocarbon effluent in the separation zone;
(g) quenching the hydrocarbon effluent once it leaves the separation zone;
(h) separating the unreacted lower number paraffin component of the hydrocarbon effluent from the hydrocarbon effluent; and
(i) recycling the unreacted lower number paraffin component back to the acceleration zone for use as at least a portion of the acceleration gas in step (a) to accelerate the fresh catalytic solids wherein the recycled lower number paraffin component first contacts the fresh, hot catalyst to allow from dehydrogenation and thermal cracking to a greater degree than the mixed feedstock thereby resulting in substantially complete dehydrogenation of each of the light paraffins wherein the reaction conditions include a kinetic residence time, from mixture of the feedstock with the catalyst to the quench, of from 0.1 to 2.0 seconds.

* * * * *

UNITED STATES PATENT AND TRADEMARK OFFICE
CERTIFICATE OF CORRECTION

PATENT NO. : 5,220,093

DATED : June 15, 1993

INVENTOR(S) : Robert J. Gartside and Axel R. Johnson

It is certified that error appears in the above-identified patent and that said Letters Patent is hereby corrected as shown below:

In Column 22, claim 1, line 4, "solid" should read --solids--.

In Column 24, claim 16, line 1, "fir" should read --for--.

Signed and Sealed this

Fifteenth Day of February, 1994

Attest:

BRUCE LEHMAN

Attesting Officer

Commissioner of Patents and Trademarks